US009096902B2

(12) United States Patent
Weier

(10) Patent No.: US 9,096,902 B2
(45) Date of Patent: Aug. 4, 2015

(54) GENETIC BARCODES

(71) Applicant: The Regents of the University of California

(72) Inventor: Heinz-Ulrich G. Weier, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/849,452

(22) Filed: Mar. 22, 2013

(65) Prior Publication Data

US 2013/0316342 A1     Nov. 28, 2013

Related U.S. Application Data

(60) Provisional application No. 61/614,456, filed on Mar. 22, 2012.

(51) Int. Cl.
    *C12Q 1/68*             (2006.01)

(52) U.S. Cl.
    CPC ............ *C12Q 1/6883* (2013.01); *C12Q 1/6841* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,427,932 A | 6/1995 | Weier et al. | |
| 5,888,730 A | 3/1999 | Gray et al. | |
| 6,066,459 A * | 5/2000 | Garini et al. | 435/6.13 |
| 2009/0098534 A1 | 4/2009 | Weier et al. | |

OTHER PUBLICATIONS

Grifo JA, Boyle A, Fischer E, Lavy G, DeCherney AH, Ward DC, Sanyal MK. Abstract Preembryo biopsy and analysis of blastomeres by in situ hybridization. Am J Obstet Gynecol. Dec. 1990;163(6 Pt 1):2013-9, Abstract only.
Grifo JA, Boyle A, Tang YX, Ward DC. Preimplantation genetic diagnosis. In situ hybridization as a tool for analysis. Arch Pathol Lab Med. Apr. 1992;116(4):393-7, Abstract only.
Speicher MR, Gwyn Ballard S, Ward DC. Karyotyping human chromosomes by combinatorial multi-fluor FISH. Nat Genet. Apr. 1996;12(4):368-75.
Cassel, M.J., Munné, S., Fung, J., Weier, H.-U.G. (1997) Carrier-specific breakpoint-spanning DNA probes for pre-implantation genetic diagnosis [PGD] in interphase cells. Hum Reprod 12:101-109.
Fung, J., Hyun, W., Dandekar, P., Pedersen, R.A., Weier, H.-U.G. (1998) Spectral Imaging in Preconception/Preimplantation Genetic Diagnosis (PGD) of Aneuploidy: Multi-Colour, Multi-Chromosome Screening of Single Cells. J Ass Reprod Genet 15, pp. 323-330.
Munné, S., Fung, J., Cassel, M.J., Márquez, C., Weier, H.-U.G. (1998) Preimplantation Genetic Analysis of Translocations: Case-Specific Probes for Interphase Cell Analysis. Human Genetics 102:663-674.

Weier, H.-U.G., Munné S., Fung J. (1999) Patient-specific Probes for Preimplantation Genetic Diagnosis (PGD) of Structural and Numerical Aberrations in Interphase Cells. Journal of Assisted Reproduction and Genetics 16:182-189.
Weier, H.U.G., S. Munné, R.A. Lersch, C. Marquez, J. Wu, R.A. Pedersen, J. Fung. (1999) High performance analysis of single interphase cells with custom DNA probes spanning translocation breakpoints. Proc. of SPIE 3604: 227-236.
Fung, J., H.U.G. Weier, J.D. Goldberg, R.A. Pedersen (1999) Simultaneous scoring of 10 chromosomes (9, 13, 14, 15, 16, 18, 21, 22, X, Y) in interphase nuclei by using Spectral Imaging. Proc. of SPIE 3604:218-226.
Fung J., Munné S., Garcia J., Kim U.-J., Weier H.-U.G. (1999) : molecular cloning of breakpoints in a case of constitutional transcolation t(11;22)(q23;q11) and preparation of probes for preimplantation genetic diagnosis (PGD). Reproduction, Fertility and Development 11, 17-23.
Weier H.-U.G., Smida J., Zitzelsberger H., Lersch R.A., Hung J., Hsieh H.P., Salassidis K., McNamara G., Pedersen R.A., Fung J. ( 2000) Cytogenetic Analysis of Interphase Cells using Spectral Imaging Technology. Proc. of SPIE 3920:76-85.
Lin, S.D., Cooper P., Fung J., Weier, H.U., Rubin E.M. (2000) Genome scan identifies a locus affecting gamma-globulin levels in human beta-cluster YAC transgenic mice. Mamm Genome 11:1024-1029.
Lersch R.A., J. Fung, S. Munné, R.A. Pedersen, H.-U.G. Weier (2000) Case-specific, breakpoint-spanning DNA probes for analysis of single interphase cells. Genetic Testing 4:273-278.
Fung J, Weier H-UG, Goldberg JD, Pedersen RA (2000) Multilocus genetic analysis of single interphase cells by Spectral Imaging. Hum Genetics 107:615-622.
Fung, J., S. Munné, H.U.G. Weier (2001) Detection of Chromosome Translocation Products in Single Interphase Cell Nuclei. Methods in Cell Biology, vol. 64, Part B, Cytometry, Third Edition (Z. Darzynkiewicz, H.A. Chrissman and J.P. Robinson, Eds.) Academic Press, San Diego, pp. 98-117.
Fung J, Weier H-UG, Pedersen RA (2001) Detection of Structural and Numerical Chromosome Abnormalities in Interphase Cells Using Spectral Imaging. J Histochem Cytochem 49:797-798.
Weier, H.-U.G., Munné, S., Lersch, R.A., Hsieh, H.B., Smida, J., Chen, X.-N., Korenberg, J.R., Pedersen, R.A., Fung J. (2001) Towards a Full Karyotype Screening of Interphase Cells: FISH and ChipTechnology. Molecular and Cellular Endocrinology 183, Suppl 1:S41-45.
Zitzelsberger HF, O'Brien B, Weier HUG (2002) Multicolor FISH techniques for the detection of inter- and intrachromosomal rearrangements. In: FISH Technology. B. Rautenstrauss and T. Liehr (Eds.), Springer Verlag, Heidelberg, pp. 408-424.
Liehr, T.; Weise, A.; Heller, A.; Starke, H.; Mrasek, K.; Kuechler, A.; Weier, H.-U.G.; Claussen, U. (2002) Multicolor chromosome banding (MCB) with YAC/BAC-based probes and regionspecific microdissection DNA libraries. Cytogenet Genome Res 97:43-50.
Weier H-UG, Weier JF, Oter Renom M, Zheng X, Colls P, Nureddin A, Pham CD, Chu LW, Racowsky C, Munné S (2005) Fluorescence in situ Hybridization (FISH) and Spectral Imaging (SIm) Analysis of Human Oocytes and First Polar Bodies. J Histochem Cytochem 53: 269-272.
Macville MV et al.,Spectral imaging of multi-color chromogenic dyes in pathological specimens. Anal Cell Pathol. 2001;22(3):133-42).

\* cited by examiner

*Primary Examiner* — James Martinell
(74) *Attorney, Agent, or Firm* — Michelle Chew Wong; Lawrence Berkeley National Laboratory

(57) ABSTRACT

Herein are described multicolor FISH probe sets termed "genetic barcodes" targeting several cancer or disease-related loci to assess gene rearrangements and copy number changes in tumor cells. Two, three or more different fluorophores are used to detect the genetic barcode sections thus permitting unique labeling and multilocus analysis in individual cell nuclei. Gene specific barcodes can be generated and combined to provide both numerical and structural genetic information for these and other pertinent disease associated genes.

12 Claims, 18 Drawing Sheets

GENETIC BARCODES

CROSS-REFERENCE TO RELATED APPLICATIONS

This application is a non-provisional of and claims priority to U.S. Provisional Patent Application No. 61/614,456, filed on Mar. 22, 2012, hereby incorporated by reference in its entirety.

STATEMENT OF GOVERNMENTAL SUPPORT

This invention was made with government support under Contract No. DE-AC02-05CH11231 awarded by the U.S. Department of Energy and under Grant Numbers CA123370A and CA132815A awarded by the National Cancer Institute and the National Institutes of Health. The government has certain rights in the invention.

REFERENCE TO TABLE APPENDIX

Table 1 is attached and hereby incorporated by reference.

BACKGROUND OF THE INVENTION

1. Field of the Invention

The present invention relates to fluorescent probes and genetic barcodes and methods for detection and analysis of gene characterization, rearrangement, translocation and expression in cancer.

2. Related Art

Our ageing population and the increasing cost of health care in all parts of the world require innovative solutions in order to be able to continue offering affordable care to all individuals. To contain the cost of care of cancer patients, for example, one approach targets the development and marketing of novel diagnostic technologies that help to stratify patient populations and identify those who would benefit from a particular treatment. This has been documented well in cases of patients with breast cancer, where estrogen and progesterone receptor status (i.e., expression levels) and amplification of growth factor receptor genes are taken into consideration, when therapeutic decisions have to be made.

In the US, the prevalence of breast cancer is roughly 100 per 100,000 (0.1%) females in any given year with a mortality rate of less than 30 per 100,000 females. While the etiology and pathogenesis of breast carcinomas remain unclear, there is overwhelming evidence that the abnormal expression of receptor tyrosine kinase genes due to gene amplification, deletions or changes in the regulation of gene expression may lead to transformation of non-malignant cells and promote tumor dissemination and invasiveness. Overexpression of the Her-2/neu protein (the product of the ErbB2 gene) and amplification of the ErbB2 gene are the most widely accepted prognostic indicator of aggressive malignant behavior of invasive breast carcinoma. Accurate detection of Her-2/neu overexpression is critical in identifying patients suitable for serotherapy with humanized monoclonal antibody (Herceptin). Fluorescence in situ hybridization (FISH) has been found to be more accurate than immunohistochemical staining using antibodies against the Her-2/neu protein.

Overexpression of another receptor tk gene, the epidermal growth factor receptor (EGFR, ERBB1) has also been shown to parallel progression to a more malignant phenotype in breast and other cancers. No diagnostic assays that allow an accurate detection of rearrangements while scoring of the number of copies of the EErbB 1 and ErbB2 genes are presently available.

In the area of Her-2/positive breast cancer, Dako's HercepTest currently leads the market. Competitors include Oncor's Inform Her-2/neu gene detection system, Vysis/Abbott PathVision's Her-2 DNA probe kits, and possibly Monogram's dimerization assay. Oncor and PathVision's products are based on fluorescence in situ hybridization detection of the Her-2/neu gene. Both tests, along with Dako's product, have been approved by the FDA.

The ErbB1 gene, coding for the epidermal growth factor-1 protein, is also know to be amplified in a subset of breast carcinomas, where is alters the cells' response to external factors among them therapeutic agents. Yet, no assay exists to test cells in a single experiment for alterations of both, ErbB1 and ErbB2, abnormalities.

BRIEF SUMMARY OF THE INVENTION

The present invention provides methods and compositions for genetic barcodes. The genetic barcodes of the invention are provided by probe sets that permit unique labeling and multilocus analysis in individual cell nuclei of multiple genes or genetic loci of interest.

In various embodiments, gene specific barcodes can be generated and combined to provide both numerical and structural genetic information for these and other pertinent disease associated genes. Gene-specific probes or genetic barcodes can be generated from publicly available database sequences and generated using probes and methods.

The probes are designed to assign typically three or more labeled probes to a gene or loci of interest. Thus in some embodiments, the gene of interest is labeled, and two other regions of genetic loci, one proximal and one distal to the gene of interest, are also labeled. The combination of the three labels in the pattern, size, arrangement and color of the labels provide the unique genetic barcode. Any detected change in the barcode is an indicator of chromosomal changes such as addition, deletion, amplification, rearrangement and/or translocation.

The presently described genetic barcodes and methods can be used to monitor and identify genetic changes. Changes to genes due to gene amplification, deletions or changes in the regulation of gene expression may lead to transformation of non-malignant cells and promote tumor dissemination and invasiveness, thus, any detectable change in the chromosome and/or gene of interest can be diagnostic or prognostic of disease occurrence, invasiveness or metastasis.

In various embodiments, an accurate and inexpensive fluorescence in situ hybridization (FISH)-based assay is provided for the detection of chromosomal changes in a gene of interest including oncogenes and the unbiased quantitation of the number of gene copies in small samples of tissue. The FISH-based technique and assay can be tailored to query alterations of other particular genetic loci of interest in cancer studies. The assay is a relatively efficient; 2 day assay and requires few cells or slide mounted tissue slices. The present FISH assay does not require the generation of metaphase spreads, which facilitates the applicability to clinical settings and in the investigation of archived tissue specimens, although in some examples, the use of metaphase spreads may enhance detection of chromosomal change by barcode detection.

Thus, the present invention also provides an accurate and inexpensive fluorescence in situ hybridization (FISH)-based assay for the detection of chromosomal changes involving either ErbB1, ErbB2 or any other oncogene and the unbiased quantitation of the number of gene copies in small samples of tissue.

The present genetic barcodes also provide unique information at a single cell level that complement current genetic assays including assays to detect chromosome abnormalities.

BRIEF DESCRIPTION OF THE DRAWINGS

FIG. 9A—Panels I, II, III and IV show BAC contig analysis of the HIPK2 locus. I) Three BAC contig probes were designed to overlap the HIPK2 locus and provide a tag for the telomeric end of chromosome 7q. II) Analysis of human lymphocytes from a normal individual shows 98% of them having the normal expected 2-2-2 pattern of the 3 contigs (arrowheads). III) Breast cancer cell line MDA-MB-468 is a heterogeneous population in which 33% of cells have a complete amplification/duplication of all three regions whereas IV) another breast cancer cell line (MDA-MB-231) is composed of 18% of cells with an extra copy of just one part (HIPK2 dist: exon 1) of the HIPK2 gene (arrow).

FIG. 9B—The genetic barcode designed for PTEN, a phosphatase that acts as a tumor suppressor, and is mutated/disrupted in a large number of cancers at high frequency. Three BAC contig probes were designed to detect Chr 10q11.21 and the distal (red) and proximal (green) ends of PTEN. An enlargement of the barcode signals detected in human lymphocyte metaphase cells are shown.

FIG. 9C—A set of barcode probes targeting the XPG/ERCC5 gene, which codes for a protein involved in repair of DNA damage. Top left: schematic diagram of probe (contigs) location along the long arm of human chromosome 13. Hybridization of the three differently labeled probe contigs on to normal human with blood cells (lymphocytes) results in the expected partially overlapping hybridization domains.

DETAILED DESCRIPTION OF THE PREFERRED EMBODIMENT

Introduction

Figure 1:
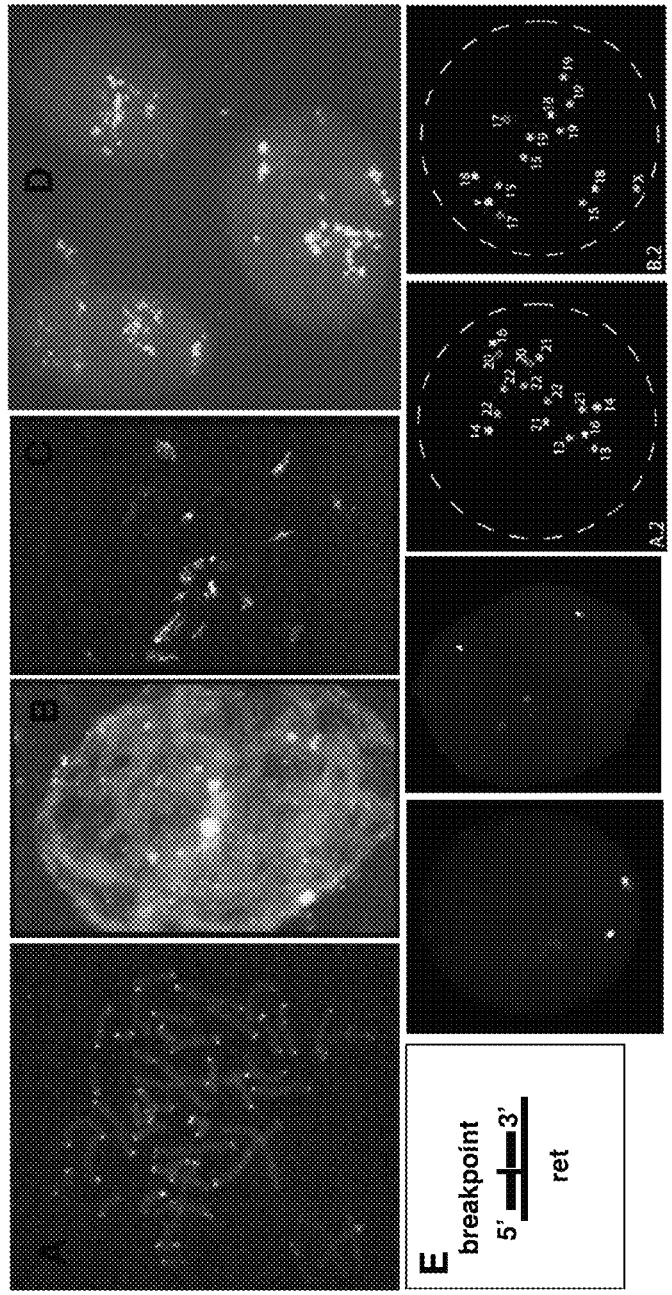
FIG. 1—Cytogenetic analysis of cells using FISH. A) Hybridization of a telomere-specific oligonucleotide probe to metaphase chromosomes results in small signals. B-C) When the same probe is hybridized to a decondensed interphase nucleus, the signal are much brighter (B=DAPI counterstain image). D) Detection of high level gene amplification in cancer cell (A-431) nuclei using an ErbB1—specific DNA probe (green spots) (red spots=chr.7 centromere). Each of the bright spots represents one copy of the gene; normal cells show only 2 signals (not shown). E) Our 2-color scheme to detect rearrangements of the ret proto-oncogene in thyroid cancer cells. We prepare differently-labeled probes that bind on opposite sides of the breakpoint (E). The barcode probes will extend this scheme by adding probes so that many more genes can be analyzed in one single experiment. F) Normal lymphocytes show the expected 2 hybridization domains with partial overlap. G) The translocation in TPC-1 cells physically separates the red and green probes. H-I) An example of perinatal diagnostic illustrating the detection of numerical chromosome aberrations in human cytotrophoblast cells by sequential hybridization. Presently, several probe sets have to be hybridized one-after-the-other to score all 24 human chromosome types. Only the results from two of the four 6-probe sets are shown for this hyperdiploid cell with a karyotype (54,XY,+6,+15,+18,+19 [2],+21,+22[2]).

Specific genomic rearrangements including translocations and gene amplification are hallmarks of many solid tumors. For example, the ErbB1 (EGFR, 7p11.2) and ErbB2 (HER2, 17q12) genes are among the most frequently amplified loci found overexpressed in cancer cells, while rearrangements such as those at the RET locus (10q11.21) are found in sporadic as well as radiation-induced papillary thyroid cancers. In research and clinical laboratories, gene amplifications are identified by either array-based or PCR-based techniques or from quantifying gene-specific (single-/dual-color) fluorescence in situ hybridization (FISH) probes in situ. On the other hand, genome-wide screening for rearrangements can be performed by FISH using chromosome painting analysis (via 'Spectral Karyotyping', SKY), if metaphase spreads are available. The members of the ErbB family often function by interacting as heterodimers, and breast cancer subtypes are classified according to the combined signaling levels of more than one receptor (ER, PR, HER2, EGFR). The lack of multiplexed assays required for the simultaneous assessment of several genetic loci in the same cell presents a major bottleneck in today's clinical analyses. Presently, there is a lack of suitable methods to analyze numerical and structural aberrations involving multiple specific loci in interphase cell nuclei.

In one embodiment, herein is described multicolor probe sets referred to herein as "barcodes" or "genetic barcodes" targeting several disease-related loci including cancer-related loci (e.g., genes such as ErbB1, ErbB2, AURKA, RET, etc.) to assess gene rearrangements and copy number changes in diseased or tumor cells. Using well-characterized bacterial artificial chromosome (BAC) clones, the probe sets can be tailored to specific applications and combinations. In some embodiments, two, three or more different fluorophores to detect the genetic barcode sections are used, thus permitting unique labeling and multilocus analysis in individual cell nuclei. The Examples and Figures show testing of these gene-specific barcodes by characterizing various established cancer cell lines in comparison to non-neoplastic cells.

In various embodiments, gene specific barcodes can be generated and combined to provide both numerical and structural genetic information for these and other pertinent disease associated genes. Gene-specific probes or genetic barcodes can be generated from publicly available database sequences and generated using probes and methods such as those described in US Patent Publication No. US-2009-0098534-A1, hereby incorporated by reference.

Instead of testing the integrity and copy number of single genes in cancer cell assays, unique color barcodes are assigned to genes and loci of interest. These barcodes are sequences of differently colored probes that bind or hybridize to genes and other chromosomal loci inside cell nuclei. In various embodiments, typically three probes are designed: one probe to detect the gene of interest; a second probe to detect a region of interest that is proximal to the gene of interest and a third probe to detect a region of interest that is distal to the gene of interest. In some embodiments, two probes are designed with one probe to detect the gene or loci of interest and a second probe to detect a second region of interest. If two probes are used as the barcode, optionally a second parameter such as size of the probe is used to uniquely label the region of interest. In some embodiments, the genetic loci contains non-protein-coding RNA and regulatory regions of the gene of interest.

Figure 10:
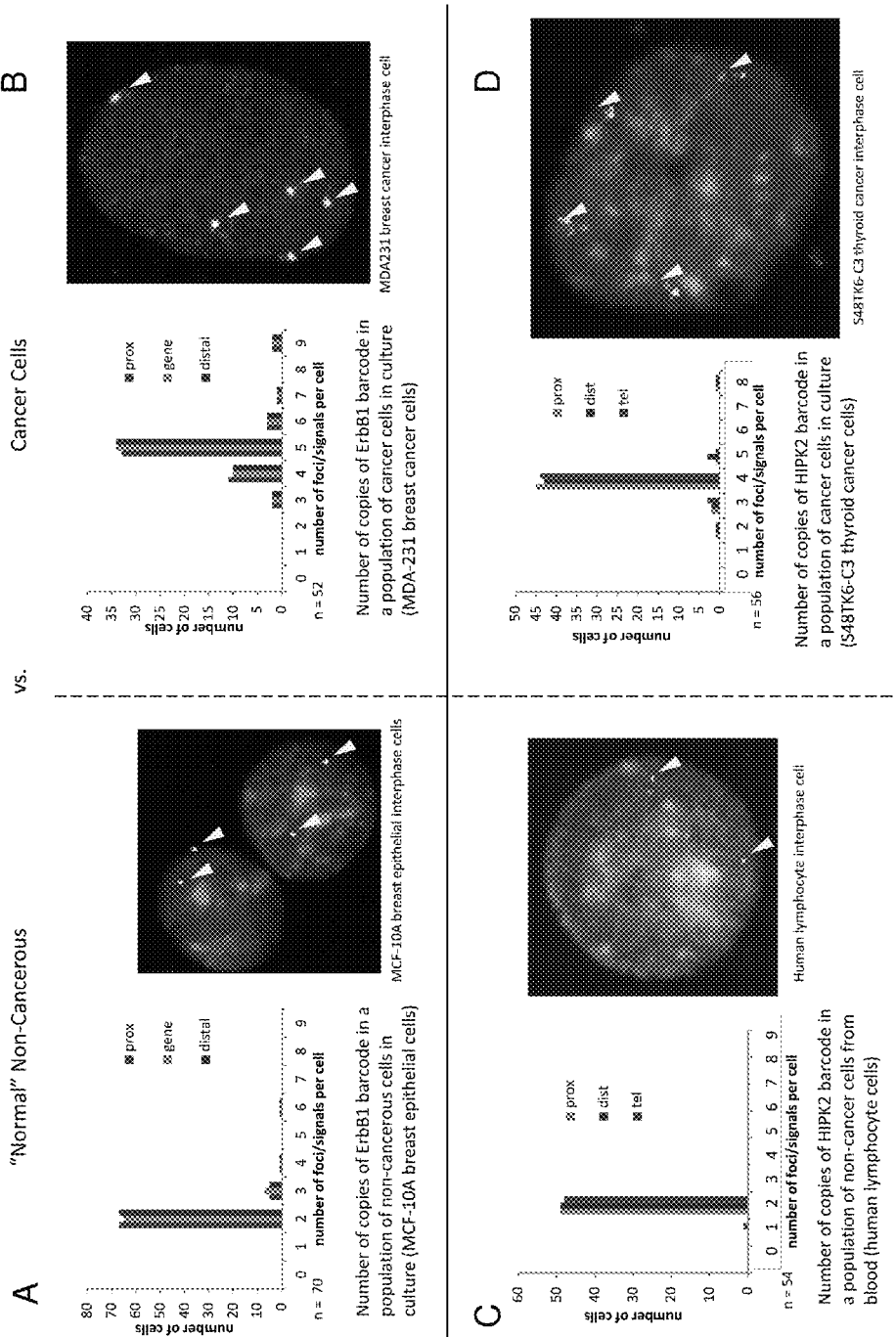
FIG. 10—Genetic barcodes are able to distinguish some diseased (cancer) from non-diseased cells. Hybridization of triple-color barcode probe sets specific for either the ErbB1 gene (top panels) or the HIPK2 gene (bottom) show the anticipated 2 copies of the entire locus in normal human lymphocytes (left panels). Cancer cells, shown to the right (MDA-231 breast cancer or S48TK6-C3 thyroid cancer cells), display 4-5 copies of these loci indicative for extra copies of the entire locus. A) "Normal" Non-Cancerous. Number of copies of ErbB1 barcode in a population of non-cancerous cells in culture (MCF-10A breast epithelial cells); B) Cancerous Cells: Number of copies of ErbB1 barcode in a population of cancer cells in culture (MDA-231 breast cancer cells); C) Lymphocyte Interphase cells: Number of copies of HIPK2 barcode in a population of non-cancer cells from blood (human lymphocyte cells); D) S48TK6-C3 thyroid cancer interphase cell: Number of copies of HIPK2 barcode in a population of cancer cells in culture (S48TK6-C3 thyroid cancer cells).
Figure 11:
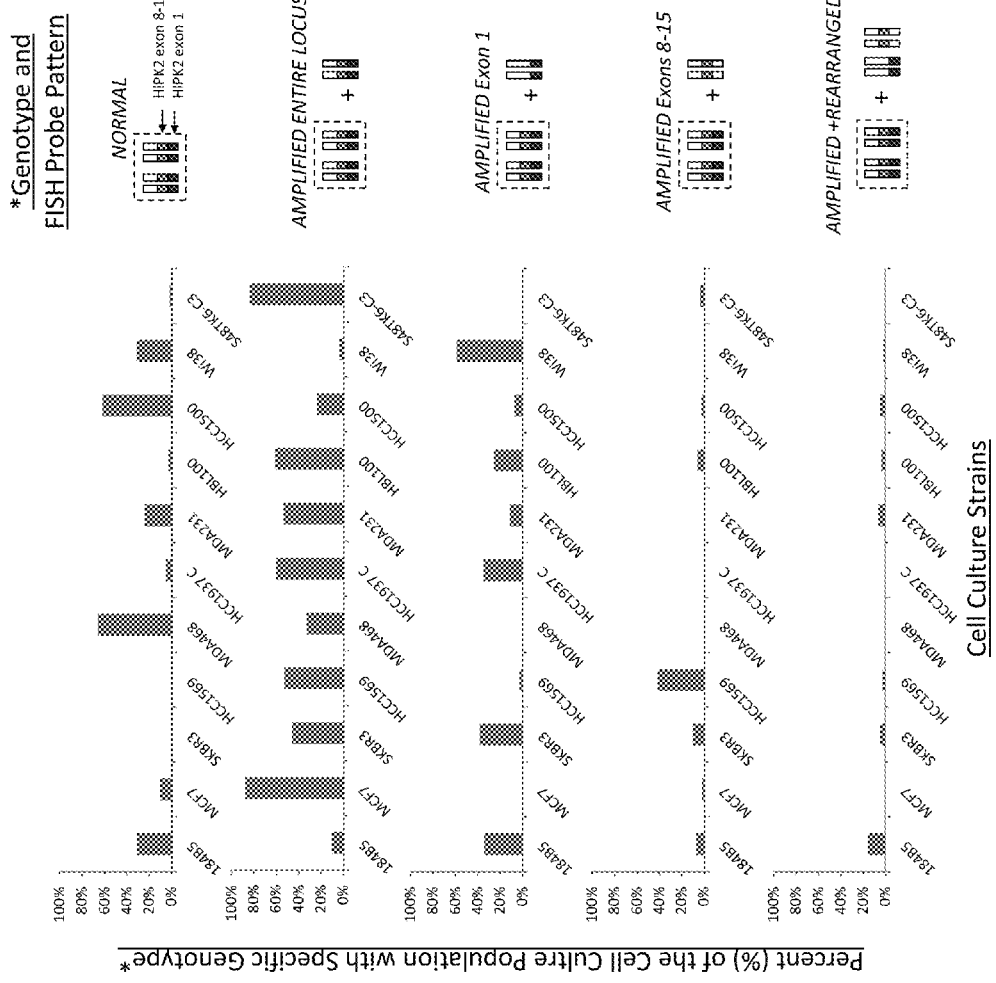
FIG. 11—Genetic barcodes are able to distinguish genetic subpopulations within a cell culture. Analysis of a panel of human breast cancer cell lines plus the thyroid cancer cell line S48TK6-C3 and normal human fibroblasts (WI-38) with the HIPK2 barcode probes reveals a spectrum of normal and rearranged gene loci. Extra copies of a rearranged HIPK2 locus (either exon 1 or exons 8-15) are present in different cell lines (bottom 3 panels), but most cell lines studied showed a complete extra copy of the entire locus (second panel from top).
Figure 12:
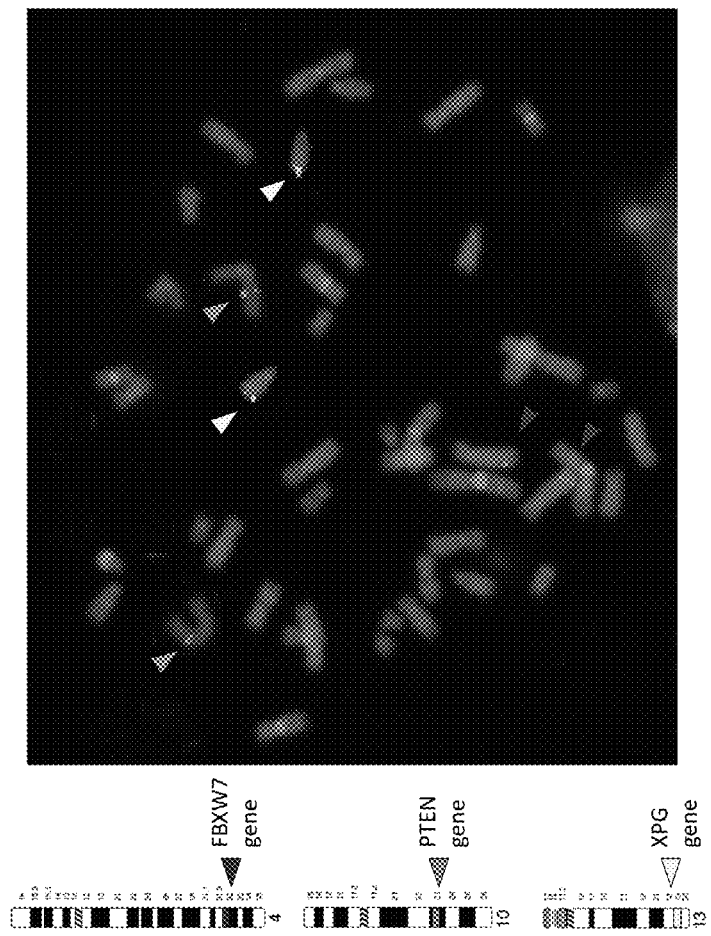
FIG. 12—Image showing analysis of 3 loci in parallel by FISH genetic barcode probes in lymphocyte (TG302B) cells.

The genetic barcode patterns, arrangements and sizes in addition to colors are detected to provide diagnostic and prognostic information regarding the patient's disease status. In various embodiments, the investigator reads the barcodes under a microscope and any change in the sequence of colored bands indicates a structural alteration of the gene as illustrated in FIG. 1 for the rearrangement of the ret gene causing human thyroid cancer. When entire genes are amplified in tumor cells, this is recognized by extra, supernumerary copies of the barcode. If a deletion occurs, the colored probe at that loci will either be missing or of a different size. If a rearrangement occurs, the sequence and location of the colored probe and of the barcode will be changed. See FIGS. 6D, 10 and 11 for examples.

The present methods and compositions also propose to solve yet another problem with multi-gene/-locus genetic analysis in cancer cells: overlapping spatial domains occupied by genes in the three-dimensional nuclei are resolved by spreading the entire DNA over a relatively large area. In some embodiments, besides physically separating the hybridization targets, spreading the DNA also results in an improved efficiency of the FISH assay (FIG. 1).

The multicolor probe contigs are prepared so that they cover the region of interest highlighting the relevant gene locations in individual, distinguishable colors. In one embodiment, a novel scheme for the detection of ErbB1/2 rearrangements in small amounts of breast tissue is based on probe contigs hybridized on to chromatin which has been released from nuclei and stretched to 140-200 micrometers, i.e., more than 10-times the normal diameter of a CA cell nucleus. Probes in addition the ErbB1/2 set probe may include reference genes, e.g., TP53, CEP1 or CEP17 and/or a collection of BAC clones that mark the chromatin between adjacent gene locations. Thus, the number of barcodes and alterations in the color sequence and/or size of signal in cells can be recorded. The assay is not limited the detection of rearrangements of ErbB 1/2 and can be applied to study conformation and copy number of any gene of interest. In another application, the scheme can be applied to score individual chromosomes in interphase cells. The proposed assay will allow the accurate analysis of very small sample sizes of cells and the detection of rearrangements (for example, the ErbB 1 and ErbB2 genes) without a requirement to grow these cells. Compared to the presently available Her-2-FISH assays or other FISH based translocation assays marketed by others (e.g., Abbott Inc.), the approach described here will screen a much larger region of either chromosome 7 or 17 for the detection of alterations that may indirectly affect the expression of the ErbB genes or other oncogenes of interest. Thus, the quantitative and structural analysis oncogenes or tumor suppressor genes is expected to provide significant support for better staging of tumors or detection of clonal alterations in circulating tumor cells providing crucial information for therapeutic decisions, prognostication and individualized therapy.

Our "genetic barcode" approach to the detection of gene rearrangements or gene enumeration is based on two basic, but crucial principles: spatial overlap between probes needs to be minimized or eliminated, and each of the gene- or chromosome-specific probes needs to be uniquely labeled and identifiable. Current approaches use sequential hybridizations with 5 probes in each set which is needed due to the unavoidable spatial overlap of hybridization domains in interphase cells, and thereby imposes a limit to 6-8 unique probe colors.

In contrast, the present methods and compositions of genetic barcodes allow the unique labeling of at least 24 genetic targets. Unique labeling using "genetic barcodes (GB's)" is achieved by preparing composite probes which uniquely label each of the targets and loci that is proximal and distal to target with specific pattern of colored "barcodes." For example, copies of ErbB1 or chromosome 7 can be identified by a red-green-orange barcode, while ErbB2 or chromosome 17 will be identified by a green-yellow-green barcode. For more examples, see FIGS. 6C, 10 and 11. In various embodiments, five to six commonly used fluorescence colors are available to design such 3-color barcodes and are more than enough to uniquely label 24 genetic targets.

In other embodiments, spatial overlap is minimized and the unique labeling of targets is increased by releasing the nuclear chromatin, i.e., DNA plus proteins, from the cell nucleus using a hypotonic buffer and detergent(s). In some embodiments, after stretching out the nuclei, the DNA is probed with all 24 probes in a single hybridization step. While present approaches make no special attempt to spread out the nuclei or increase hybridization efficiencies, this is expected to greatly expedite the procedure. The methodologies described herein address the overlap issue problems and, at the same time, enhance access of probes to DNA targets.

Specific probes and their preparation that may be used in the probe sets of the invention include those described by Weier, H.-U., Kleine, H.-D., Gray, J. W. (1991) Labeling of the centromeric region on human chromosome 8 by in situ hybridization. *Human Genetics* 87:489-494 and Weier, H.-U., Rosette, C. D., Matsuta, M., Zitzelsberger, H., Matsuta, M., Gray, J. (1994) Generation of highly specific DNA hybridization probes for chromosome enumeration in human interphase cell nuclei: isolation and enzymatic synthesis of alpha satellite DNA probes for chromosome 10 by primer directed DNA amplification, *Meth Mol Cell Biol* 4:231-248, along with those described in the References listed herein, which are herein incorporated by reference. One of skill in the art could select other probes to the target genes.

In another embodiment, other probes can also be developed according to known procedures in the art, briefly described herein. Methods of preparing probes are well known to those of skill in the art (see, e.g. Sambrook et al., Molecular Cloning: A Laboratory Manual (2nd ed.), Vols. 1-3, Cold Spring Harbor Laboratory, (1989) or Current Protocols in Molecular Biology, F. Ausubel et al., ed. Greene Publishing and Wiley-Interscience, New York (1987)), which are hereby incorporated by reference.

Another example of a method that can be used to develop probes for the present hybridization analysis is found in U.S. Pat. Nos. 5,427,932 and 5,888,730, and Cassel, M. J., Munné, S., Fung, J., Weier, H.-U. G. (1997), Carrier-specific breakpoint-spanning DNA probes for pre-implantation genetic diagnosis [PGD] in interphase cells. *Hum Reprod* 12:101-109, all of which are hereby incorporated by reference. The method as applied to development of probes for determination of chromosomal abnormality can be as follows. The probes are most easily prepared by combining and labeling as described herein.

Prior to use, larger constructs can be fragmented to provide smaller nucleic acid fragments that easily penetrate the cell and hybridize to the target nucleic acid. Fragmentation can be by any of a number of methods well known to those of skill in the art, including random priming, nick translation, and tailing. Treatment of larger size probes include sonication, or enzymatic restriction to selectively cleave the molecule.

Probes are preferably fragmented to or are made with an average fragment length ranging from about 50 bp to about 2000 bp, more preferably from about 100 bp to about 1000 bp and most preferably from about 150 bp to about 500 bp. However, there is no maximum or minimum size required of the present genetic barcode probes in order to allow the design of unique barcodes that detect and score small to large changes such as deletions of non-coding regions, large repeat changes, partial up to whole chromosome arm deletions or changes in large non-protein coding intergenic regions.

Preferred probes include DNA double-stranded probes, which may require denaturation, alkaline treatment or exonuclease digestion, single-stranded DNA probes and oligonucleotides, RNA probes or peptide nucleic acid (PNA) probes. All DNA and RNA probes can be prepared by nick translation or random priming with commercial kits (such as BIOPRIME, BIONICK available from Invitrogen). Synthetic oligonucleotide probes can prepared and obtained commercially. Methods of making and using PNA probes are described in Peter E. Nielsen, ed., Peptide Nucleic Acids: Protocols and Applications (Second Edition), Horizon Bioscience, The Panum Institute, Copenhagen, January 2004, hereby incorporated by reference.

Each set of probes should be prepared with similar hybridization parameters and blocking requirements. In general, single copy probes like those prepared from BAC or YAC clones require blocking of interspersed repeat (LINEs, SINEs), which is commonly achieved by addition of unlabelled COT1 (Life Technologies) DNA. The COT1 DNA contains just the highly repeated DNA sequences such as SINEs, LINEs, ALUs and satellite DNA. In some applications it is necessary to block the hybridization capacity of repetitive sequences. In one embodiment, human genomic DNA is used as an agent to block such hybridization. The preferred size range is from about 200 bp to about 1000 bases, more preferably between about 400 to about 800 bp for double stranded, nick translated nucleic acids.

Probes that target DNA repeats, on the other hand, can often be prepared highly specifically and do need minimal or no blocking prior to or during hybridization. Thus, single copy and DNA repeat probes are best used separately. It would be preferred that the hybridization strategy be applied to a set of 6-8 locus-specific bacterial artificial chromosome (BAC) or yeast artificial chromosome (YAC) probes first because BAC probes target 100-300 kb and target sizes for YAC derived probes can exceed 1 megabase. In some embodiments, clones are selected that produce tightly localized hybridization domains in interphase cells, which will be easy to score. In one embodiment, after clone selection, hybridizations are performed in the presence or absence of human COT1 blocking DNA to estimate the amount of cross-hybridization caused by various types of DNA repeats in the single copy BAC or YAC probes.

The selection of probe clones can be guided by quite a number of rules. Examples for such rules are the inclusion/exclusion of probes for highly repeated DNA targets. Some of these probes bind to DNA targets (pericentromeric heterochromatin, satellite DNA, etc.) that are heteromorphic. Thus, an individual might carry one chromosome with a large target leading to a strong signal, while the other homologue carries a much smaller repeat cluster. In extreme, but not very rare cases, the difference might be so drastic that (especially when the hybridization efficiency is compromised) only the strong signal is scored by the observer. Thus, to understand the consequences of using heteromorphic FISH targets one has to keep in mind that in some of the clinical investigations only a single cell or sample will be available for analysis.

In a preferred embodiment, detection of the hybridization events can be carried out and the genetic barcodes are identified using in situ hybridization. Generally, in situ hybridization comprises the following major steps: (1) isolating and fixation of the single cell or biological structure containing the target chromosomes to analyzed; (2) prehybridization treatment of the cell or biological structure to increase accessibility of target DNA, and to reduce nonspecific binding; (3) hybridization of the mixture of probes to the target chromosomes in the biological structure or cell; (4) posthybridization washes to remove unbound probes and posthybridization treatment such as washes, blocking, detection and amplification; and (5) detection of the hybridized probes. The reagent used in each of these steps and their conditions for use may vary depending on the particular application.

For example, fixation of the single cell can include the steps of first immersing the cell in a drop of hypotonic solution, e.g., 75 mM KCl, to allow the cell to swell and cover a larger area. A fixative, such as acetic acid:methanol 1:3 v/v, can be pipetted onto the cell to hydrolyze proteins, remove hypotonic solution, and fix the cell to untreated glass slides. Treatment with RNAase is also recommended before or after fixation. Other post-fixation treatments can include enzymatic pretreatments, post fixation washes in buffers of different salt concentration, secondary fixation using paraformaldehyde or acetone for example, and incubation at elevated temperature (e.g. in ambient temperature in air for 2 weeks or 80° C. for 1-2 hours) which acts as a method of aging to retain DNA throughout further denaturation and hybridization steps.

Prior to contacting the probes with the single cell or the organelles to hybridize the probes, a denaturation step can be performed thermally or chemically, but is only necessary if DNA double-stranded (ds) probes are selected. After hybridization of the probes to the target chromosomes in the single cell or organelle, any number of posthybridization treatments can occur. These can include, but are not limited to, posthybridization washes to remove unbound probes and post hybridization processing such as washes, blocking, detection and amplification. Finally detection of the hybridized probes can be carried out. In a preferred embodiment, the detection of the probes is performed using a filter-based fluorescent microscope, optionally equipped with a spectral imaging system.

Filter-Based Fluorescent Microscope. In a preferred embodiment, the probes selected are fluorescent probes thereby allowing the detection of the hybridized probes using a filter-based fluorescent microscope. In a preferred embodiment, the microscope is equipped with a CCD camera and fluorescent filters, such as FITC or Texas Red filters, for fluorochrome excitation and observation. In a preferred embodiment, the multiple band pass filter set (ChromaTechnology, Brattleboro, Vt.) can be used for fluorochrome excitation to provide three broad emission bands centered around 470 nm, 565 nm and 640 nm. Fluorescence can be recorded through a multi-bandpass filter with broad transmission peaks in the vicinities of 520 nm (green), 600 nm (red) and 700 nm (infrared) (Schroeck et al., 1996) to match the excitation/emission profile of the selected fluorochromes. In one embodiment, the microscope has a combination of eight excitation/emission filters for the eight dyes used for each 8-probe set such as DAPI, Spectrum Aqua or Pacific Blue and the CCD camera.

One detection strategy is based on interchangeable excitation and fluorescence emission filters termed multi-fluor FISH or mFISH which is described by Speicher M R, Gwyn Ballard S, Ward D C. Karyotyping human chromosomes by combinatorial multi-fluor FISH. *Nat Genet.* 1996 April; 12(4):368-75, which is hereby incorporated by reference.

Filter-Based Fluorescent Microscope with Spectral Imaging (SIm) System. In another preferred embodiment, the hybridized fluorescent chromosome-specific probes are detected using a filter-based fluorescent microscope with a spectral imaging system. A recent development in fluorescence microscopy termed 'Spectral Imaging (SIm)' now allows the recording of an entire spectrum from a fluorescent object with high resolution. Existing SIm instrumentation can record fluorescence spectra from 400 nm to 1100 nm with about 10 nm resolution and has been described by Schröck et al., (1996) Multicolour spectral karyotyping of human chromosomes. *Science* 273: 494-497; Liyanage et al., Multicolour spectral karyotyping of mouse chromosomes, *Nat Genet.* 1996 November; 14(3):312-5 1996; Garini et al., Spectral karyotyping. *Bioimaging* 4, 65-72 (1996); Fung et al., Spectral imaging in preconception/preimplantation genetic diagnosis of aneuploidy: multicolor, multichromosome screening of single cells, *J Assist Reprod Genet.* 1998 May; 15(5):323-30, which are hereby incorporated by reference. In a preferred embodiment, the spatial resolution, limited by the diffraction in the light microscope, is typically better than 500 nm.

Typically, SIm combines the techniques of fluorescence microscopy, charge-coupled device (CCD) camera and Fourier spectroscopy (FIG. 1). The light emitted from each point of the sample is collected with the microscope objective and sent to a collimating lens. The collimated light travels through an optical head (interferometer) and is focused on a charged coupled device (CCD). The data are collected and processed with a personal computer. The interferometer divides each incoming beam (the light projected from the microscope) into two coherent beams and creates a variable optical path difference (OPD) between them. The beams are then combined to interfere with each other, and the resulting interference intensity is measured by the CCD detector as a function of the OPD. The intensity vs. OPD is called 'an interferogram'. The spectrum, i.e., intensity as function of wavelength, can be recovered from the interferogram by a relatively simple mathematical operation called 'Fourier transformation'. This transformation is performed in the personal computer attached to the Spectral Imaging system. The spectral resolution depends on the number of interferometric steps. For most experiments, a resolution of 10-20 nm (equivalent to 64-128 steps) is sufficient.

First applications of SIm, also termed 'Spectral Karyotyping (SKY),' screened metaphase spreads for translocations. See Schröck et al. 1996; Zitzelsberger et al., Cytogenetic changes in radiation-induced tumors of the thyroid, *Cancer Res.* 1999 Jan. 1; 59(1):135-40; Zitzelsberger et al., Clonal chromosomal aberrations in simian virus 40-transfected human thyroid cells and in derived tumors developed after in vitro irradiation, *Int J. Cancer.* 2001 Jun. 20; 96(3):166-77; Weier, H. U. G., S. Munné, R. A. Lersch, C. Marquez, J. Wu, R. A. Pedersen, J. Fung. (1999) High performance analysis of single interphase cells with custom DNA probes spanning translocation breakpoints. *Proc. of SPIE* 3604: 227-236; Fung, J., H. U. G. Weier, J. D. Goldberg, R. A. Pedersen (1999) Simultaneous scoring of 10 chromosomes (9, 13, 14, 15, 16, 18, 21, 22, X,Y) in interphase nuclei by using Spectral Imaging. *Proc. of SPIE* 3604:218-226.

Based on these first applications, some embodiments allow hybridization of the human chromosomes with chromosome-specific whole chromosome painting (WCP) probes labeled individually with Spectrum Green, Spectrum Orange, Texas Red, Cy5, or Cy5.5 and combinations thereof, for rapid analysis of interphase or metaphase spreads in a single experiment.

In a preferred embodiment, using a Xenon light source, the spectral image is generated by acquiring 80-130 interferometric frames per object. The sample emission spectra (400-850 nm) can be measured simultaneously at all points in the microscopic image. The spectral information is displayed by assigning specific colors, e.g., red, green or blue, to certain ranges of the spectrum. This display, e.g., an RGB display, renders chromosomes that were labeled with spectrally overlapping fluorochromes or fluorochrome combinations in a similar color. Based on the measurement of the pure spectrum for each chromosome a spectral classification algorithm is applied to allow the assignment of a pseudo-color to all pixels in the image that have the same fluorescence spectrum. Chromosome identification is then performed by comparison of the measured spectra with pre-recorded reference spectra, and chromosomes are displayed in 'classification' colors to facilitate the detection of translocations involving non-homologous chromosomes in SKY analyses of metaphase spreads or the loss of chromosomes or detection of extra chromosomes in SIm analysis of interphase cells. See J. Fung et al., Multilocus genetic analysis of single interphase cells by spectral imaging, *Hum Genet.* 2000 December; 107(6):615-22 hereby incorporated by reference.

In some embodiments, the fluorescence spectra of the reporter molecules should have minimal overlap. In other embodiment, the spectra of the reporter molecules may be partially overlapping, as spectral overlap can be resolved by 'Spectral Un-Mixing (SUN)' (developed by ASI; see also Macville MV et al., Spectral imaging of multi-color chromogenic dyes in pathological specimens. *Anal Cell Pathol.* 2001; 22(3):133-42). Images are imported and analyzed after being recorded with either the Spectral imaging system or a combination of excitation/emission filters for dyes such as DAPI, Spectrum Aqua or Pacific Blue and the CCD camera.

Figure 2:
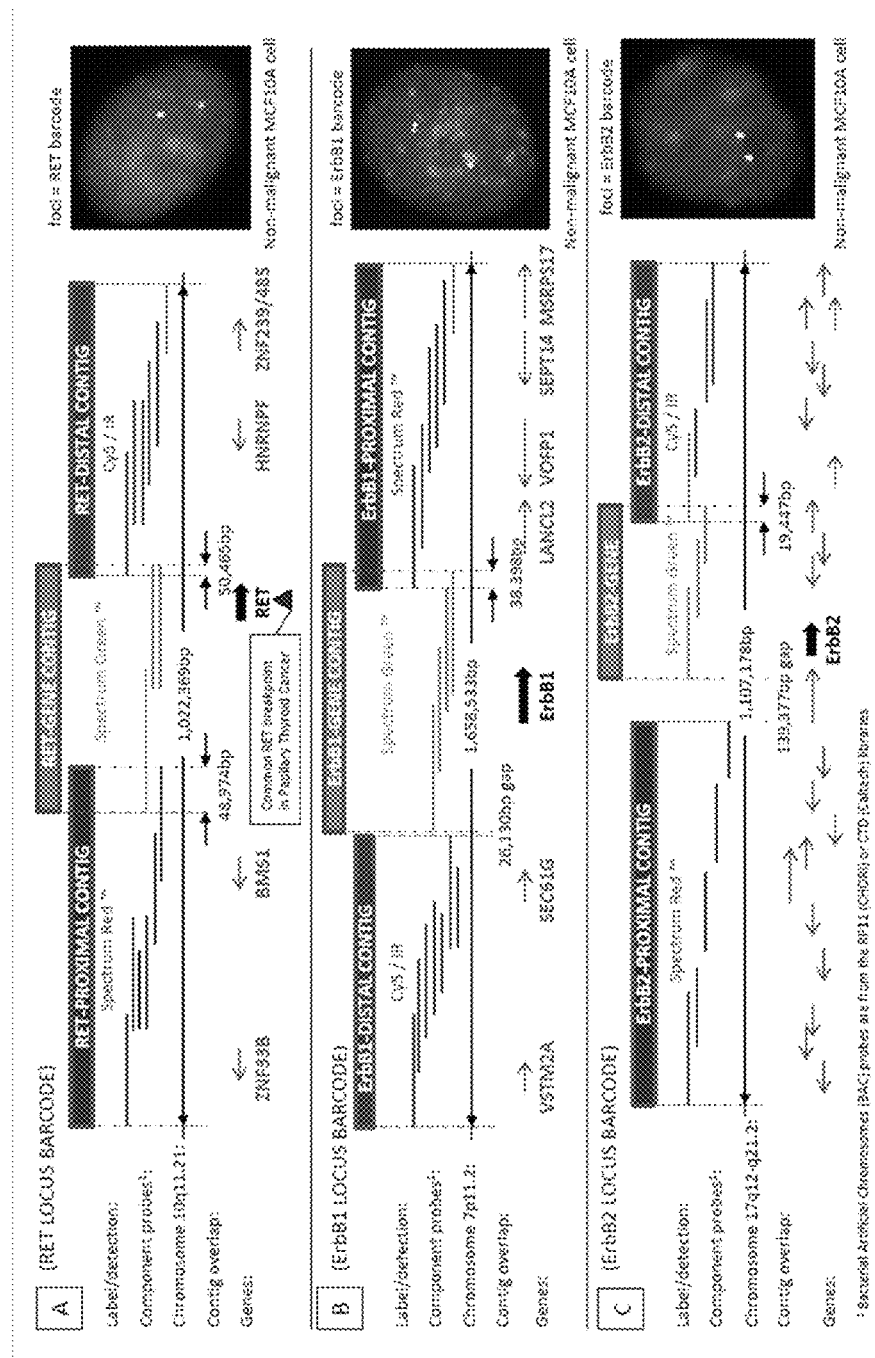
FIG. 2—Design of the barcodes for 3 gene loci (A) RET, (B) ErbB1 and (C) ErbB2. Each has 3 components, a proximal, gene and distal contig, all individually labeled to be distinguishable by IF. Inset on right shows the 3 colour staining pattern for each contig set in cells expected to have non-rearranged loci.

In another embodiment, chromosomal make-up of single cells or cell organelles are detected using the spectral imaging methods (SIm) as described above, because of the high spectral resolution of SIm. As mentioned above, the ratio-labeling color scheme applied for SKY will not work for the determination of the intracellular number of chromosomes, because the different hybridization targets could spatially overlap. Therefore, in a preferred embodiment, each DNA probe is labeled with a unique reporter molecule. In one embodiment, the reporter molecule is a fluorochrome that is commercially available. Their emission maxima should be spaced sufficiently to allow discrimination by a Spectral Imaging or filter based system. For example, FIG. 2 shows a scheme to uniquely label multiple chromosome-specific hybridization targets and counterstain genomic DNA and having their emission maxima spaced sufficiently to allow discrimination by a Spectral Imaging system.

Other Applications. It is further contemplated that the probe set can be optimized with regard to probe specificity, signal strength, ease of use and cost, according to the teachings of the invention and using methods known in the art.

Clinical cancer diagnostics with its wealth of already identified disease markers will be an important, but not the sole application of the multiplexed 'genetic barcoding'. For example, future applications will extend into the field of peri-natal diagnosis by scoring all human chromosome types in a single test. FIG. 1 H-I illustrate the present state of chromosome enumeration in individual cells, where several sets of chromosome-specific probes have to be hybridized sequentially to score all 24 chromosome type and identify abnormal cell or embryos.

EXAMPLE 1

Using Genetic Barcodes to Detect ER Status in a Panel of Cancer Cell Lines

Probes to ErbB1 gene and the proximal and distal regions were made from BAC probes from the RP11(CHORI) or CTD (Caltech) libraries. Methods to make such probes are described above and in International application WO 2006/091979, which is US Patent Publication No. US-2009-0098534-A1, hereby incorporated by reference.

Figure 3:
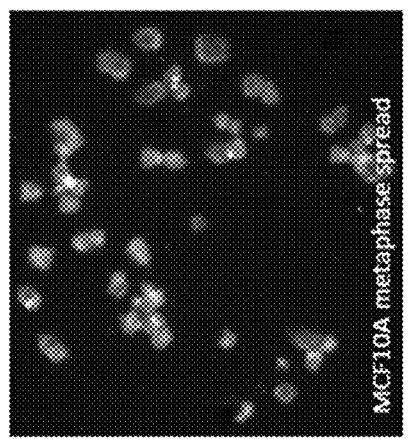
FIG. 3—Example of a FISH barcode staining pattern in 'normal' non-malignant cells. A) MCF10A cells have 2 foci of the ErbB1 barcode with each foci containing each component contig, B) each of the foci is clearly on a separate chromosome and C) the predominant (86% of cells) pattern in the culture is 2 foci.
Figure 3:
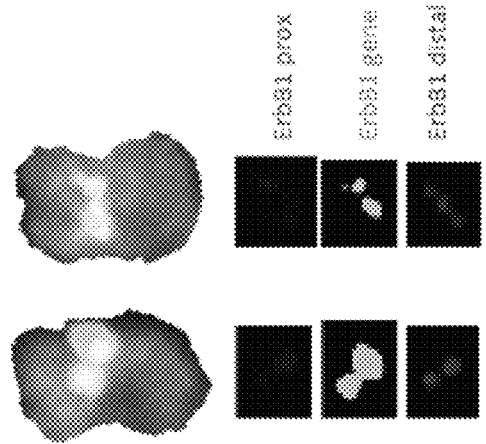
Figure 3:
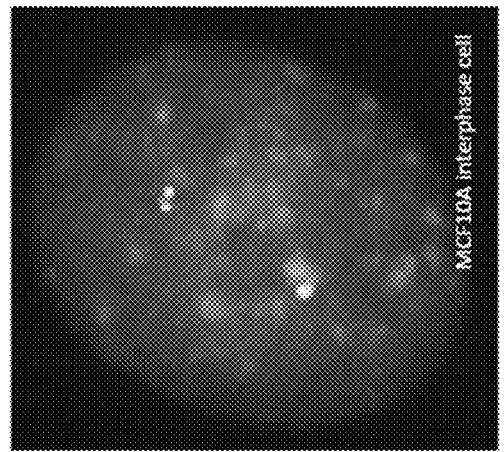
Figure 3:
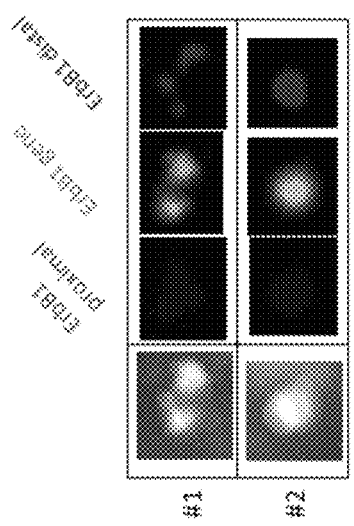
Figure 3:
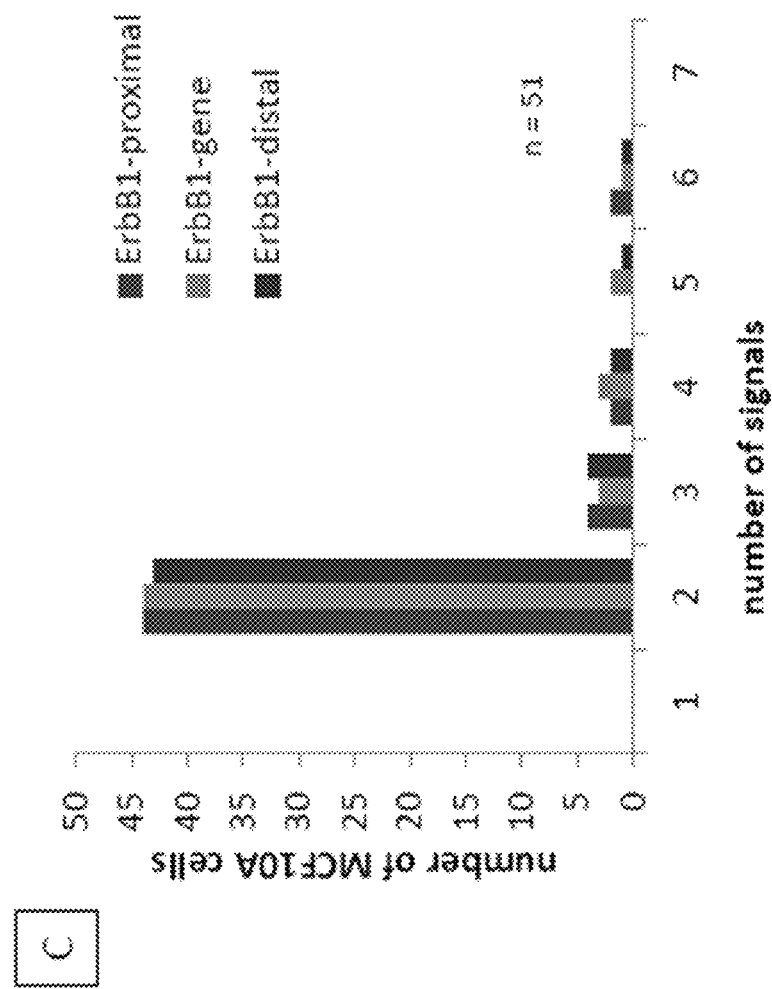

Detection of specific abnormalities and DNA probes preparation was a carried out in cancer cell lines. In FIG. 3, a FISH barcode staining pattern in MCF10A non-malignant cells. MCF10A cells were shown to have 2 foci of the ErbB1 barcode with each foci containing each component contig, with each of the foci clearly on a separate chromosome and the predominant (86% of cells) pattern in the culture is 2 foci.

Figure 4:
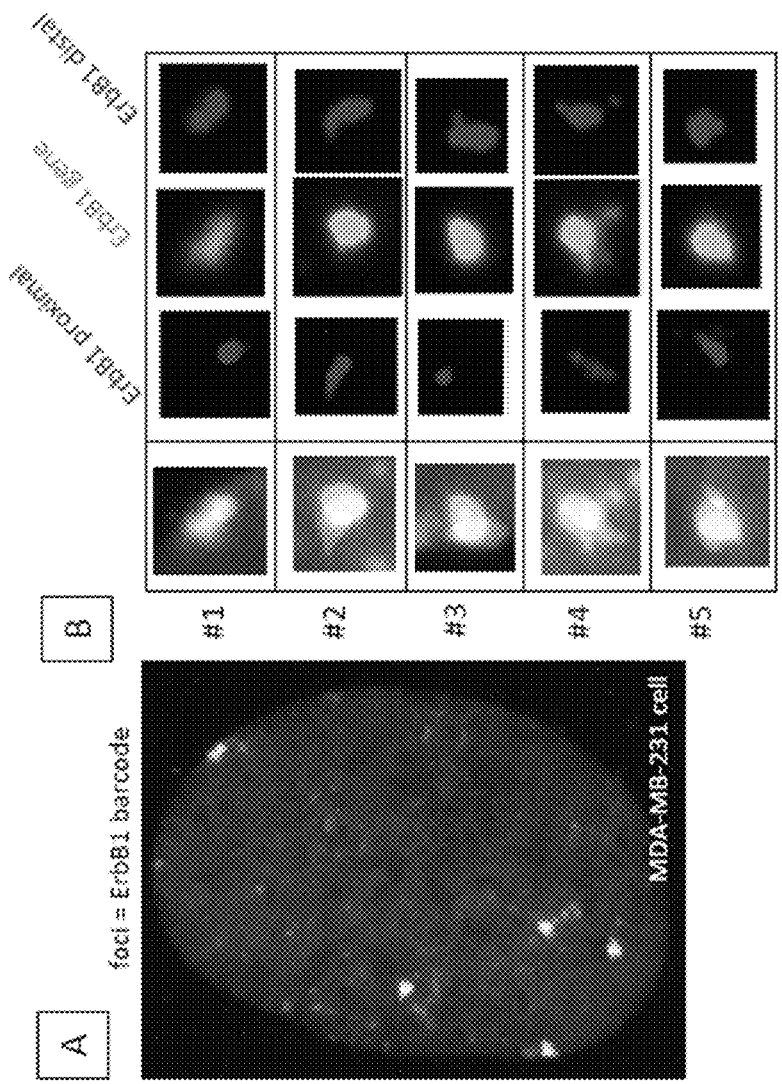
FIG. 4—Examples of genetic amplifications/translocations identified by a genetic barcode in cancer cells. A) MDA-231 cells have 5 foci identified by the ErbB1 barcode, B) each foci contains (at least part) of each contig C) each is a locus clearly on separate chromosomes and D) the predominant (58% of cells) pattern in the culture is 5 foci.
Figure 4:
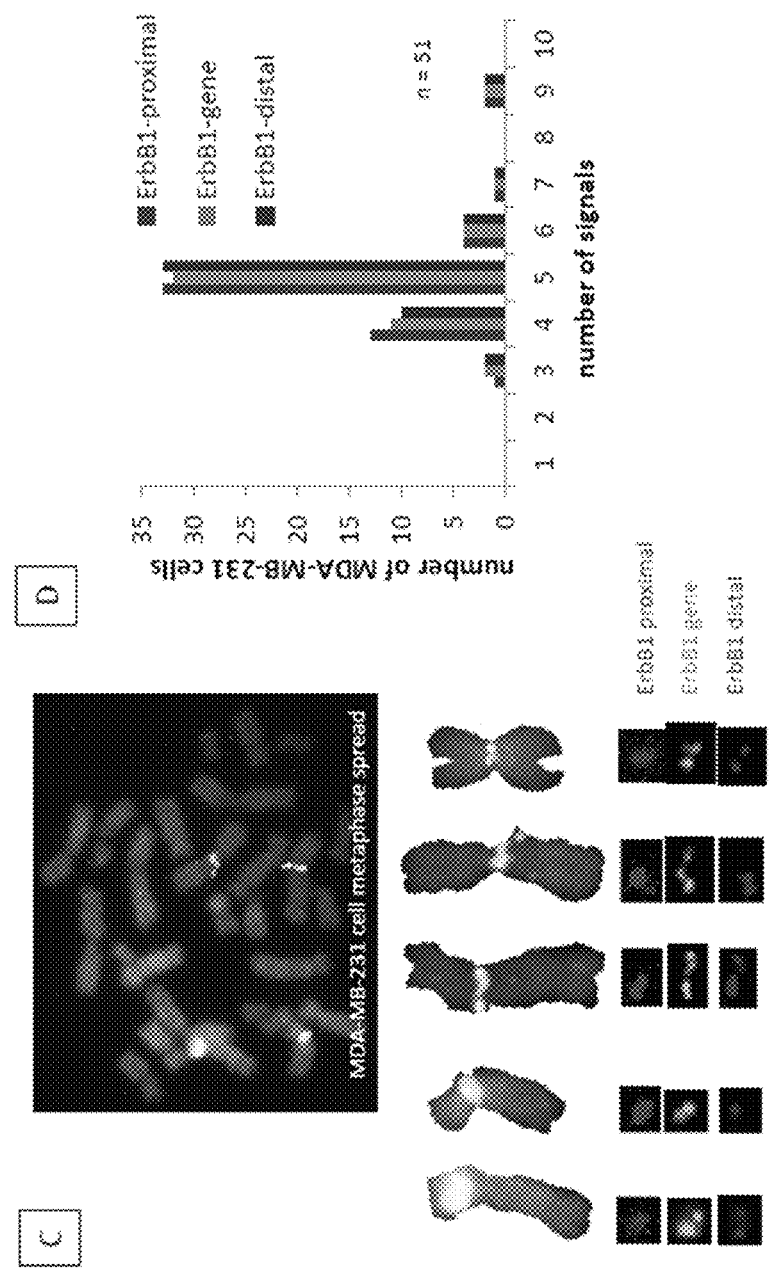

Referring now to FIG. 4 genetic amplifications/translocations were identified by a genetic barcode in cancer cells. MDA-231 cells have 5 foci identified by the ErbB1 barcode, with each foci containing (at least part) of each contig. Each is a locus clearly on separate chromosomes and the predominant (58% of cells) pattern in the culture is 5 foci.

Figure 5:
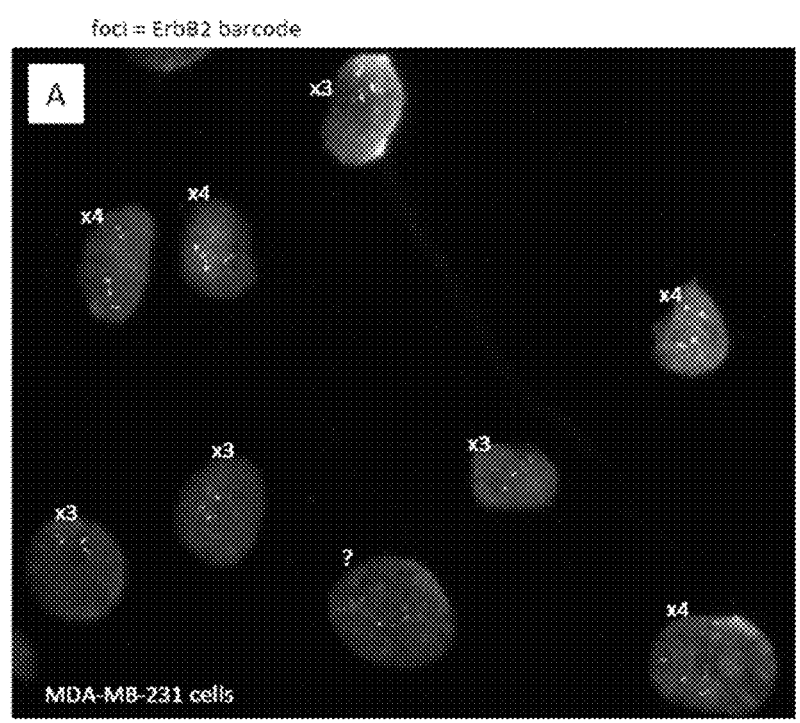
FIG. 5—Example of genetically heterogeneous populations identified by a genetic barcode. A) MDA-231 cells have various patterns of ErbB2 foci, B-1) some have 3 foci, B-2) some have 4 foci containing (at least part of) each ErbB2 contig and C) there are about 45-47% of each cell genotype in the culture.
Figure 5:
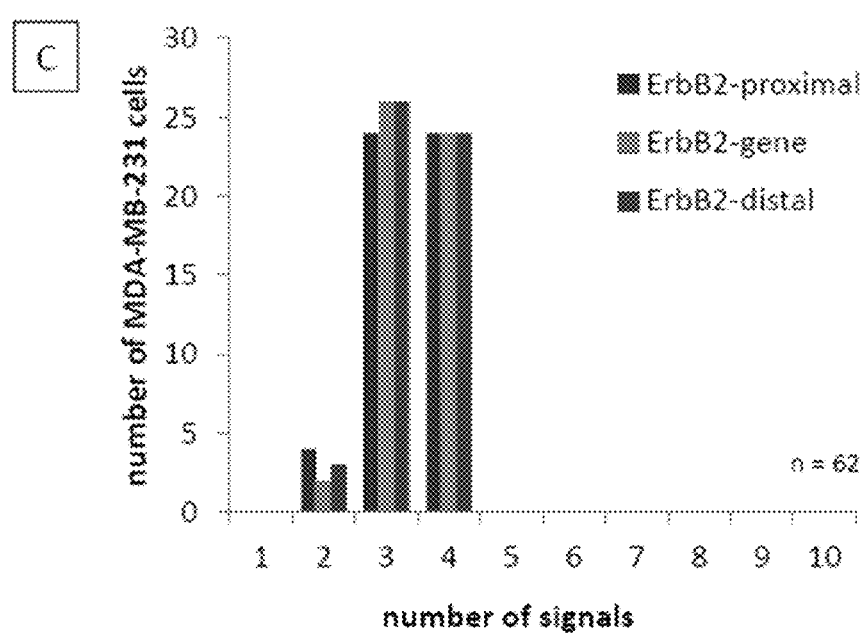
Figure 5:
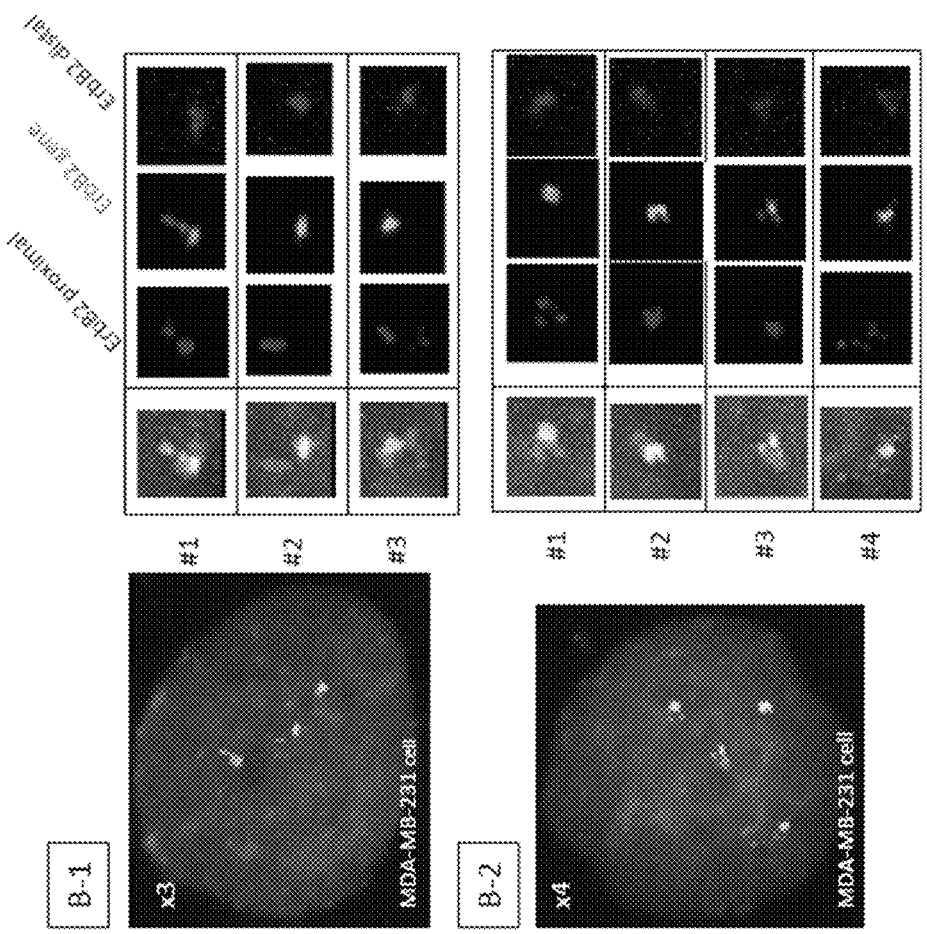

Referring now to FIG. 5 MDA-231 cells have various patterns of ErbB2 foci: some have 3 foci, and some have 4 foci containing (at least part of) each ErbB2 contig and there are about 45-47% of each cell genotype in the culture.

Figure 6:
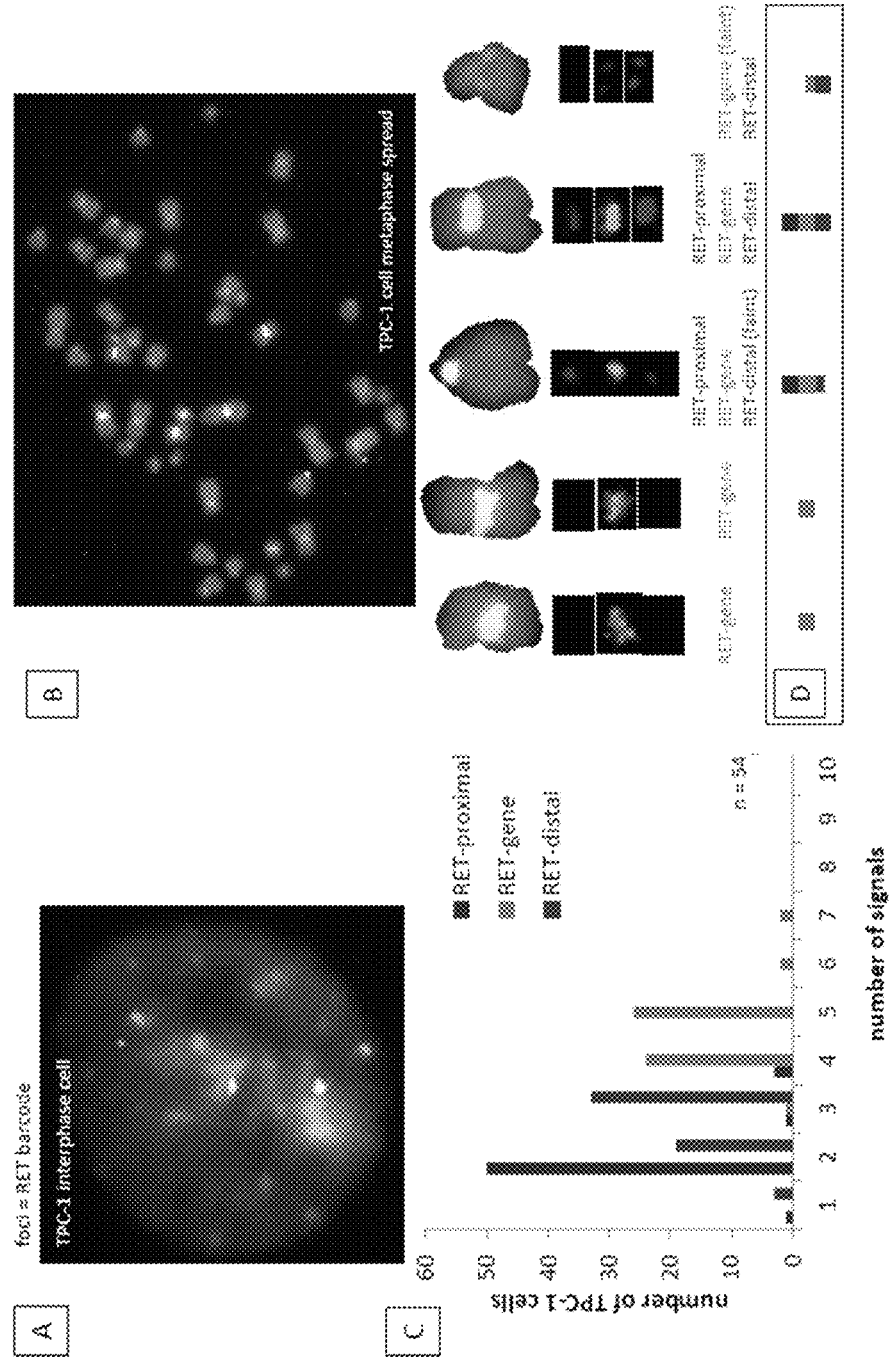
FIG. 6—Example of a complex locus rearrangement as observed with a genetic barcode in cancer cells. A) TPC-1 cells have a complex pattern of RET barcode foci, B) each of the foci is on an individual chromosome, C) the predominant pattern has 2 proximal contigs +4-5 gene contigs +2-3 distal contigs and D) shows our interpretation of the contig arrangement across the various chromosomes.
Figure 7:
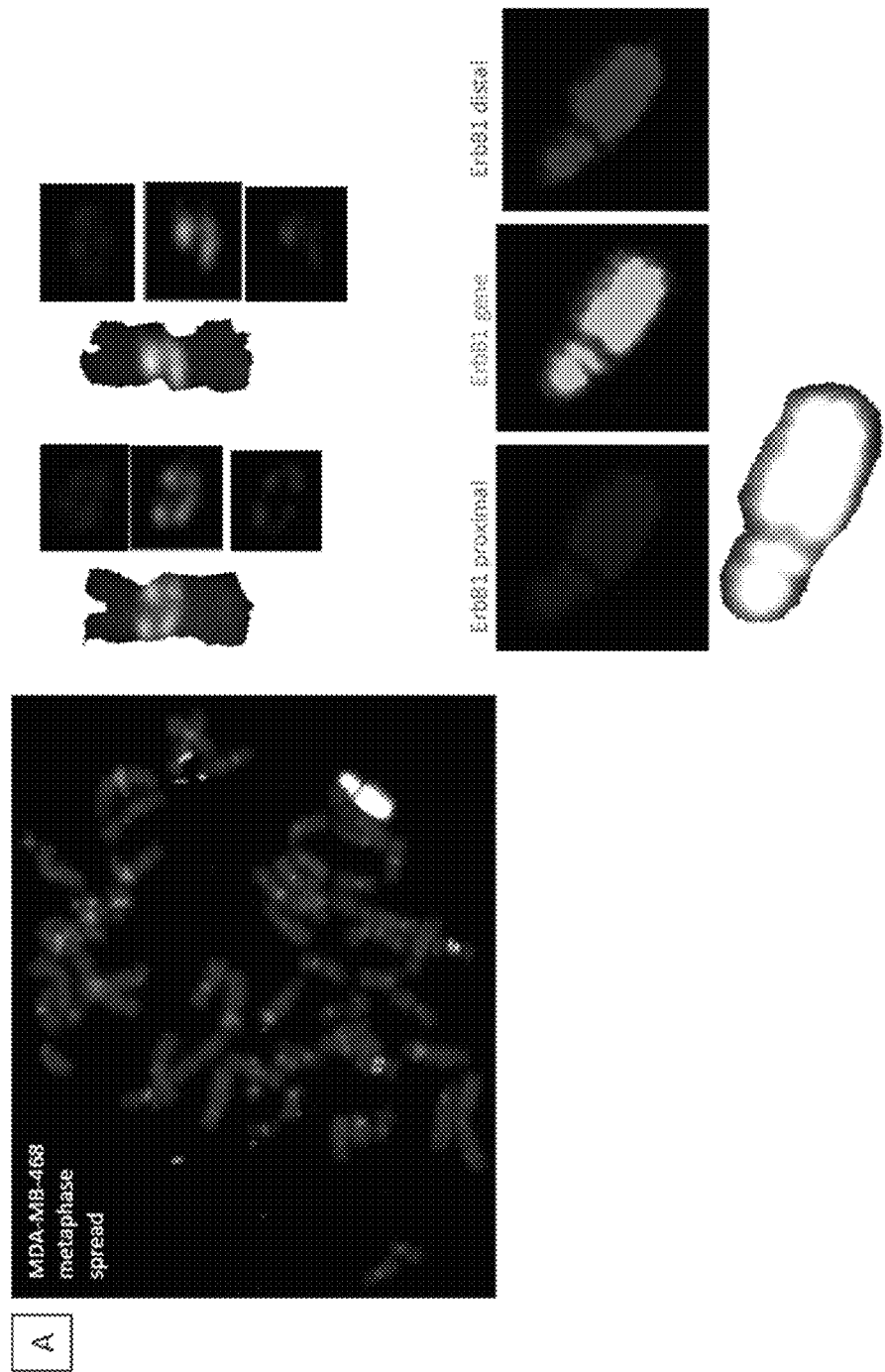
FIG. 7—Example of high level amplification of a locus observed by a set of genetic barcode probes in cancer cells. A) MDA-MB-468 cells show extensive amplification of the ErbB1 locius, containing at least 80-100 copies of each set of probe contigs (1.65 Mbp total length), it also appears incorporated along the length of one entire chromosome. B) The pattern is harder to distinguish in interphase cells.
Figure 7:
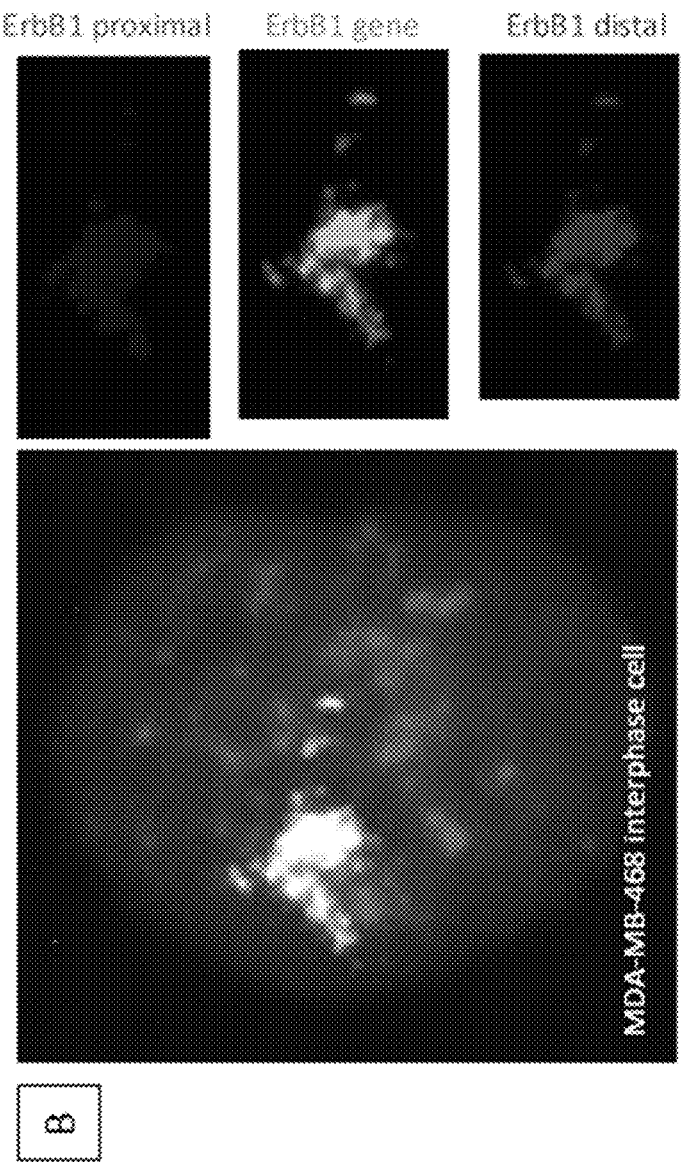
Figure 8:
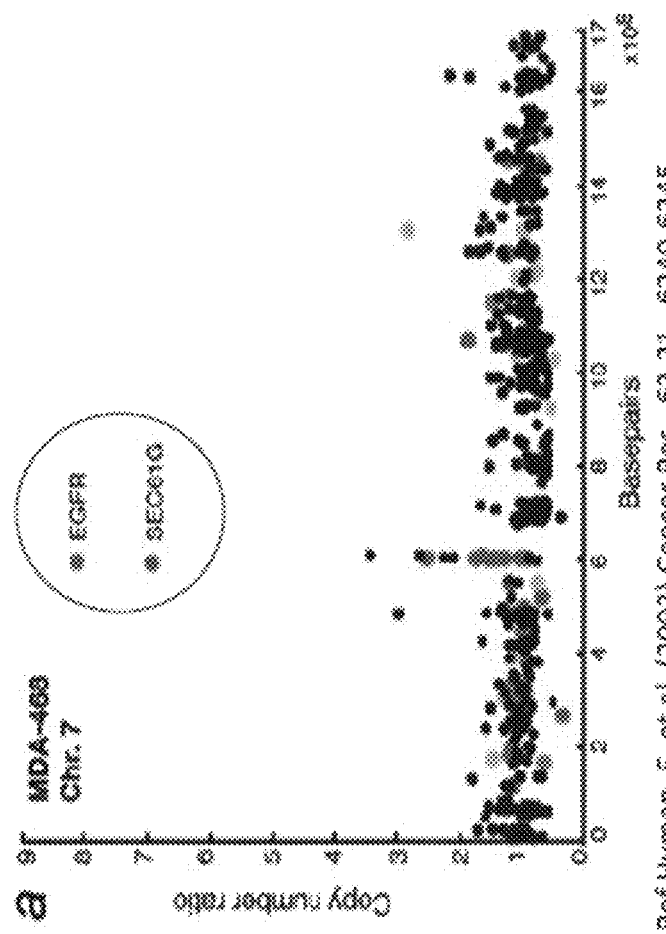
FIG. 8—Array CGH has also identified an increased copy number of the ErbB1 gene region in MDA-MB-468 cells.

Referring now to FIG. 6, complex locus rearrangements are observed with a genetic barcode in cancer cells. FIG. 6D shows our interpretation of the contig arrangement across the various chromosomes. FIG. 7 shows an example of extensive amplification of the ErbB 1 locus in MDA-MB-468 cells, containing at least 80-100 copies of each set of contigs (1.65 Mbp total length), it also appears incorporated along the length of one entire chromosome. This observation of increased detection of gene amplification by the FISH correlates with Array CGH data which also identified an increased copy number of the ErbB 1 gene region in MDA-MB-468 cells (FIG. 8).

EXAMPLE 2

Using Genetic Barcodes to Detect ER Status in a Patient Biopsy

Present work focuses on the development of clinical assays for the detection and characterization of genetic alterations in tumor cells, and investigation of a potential correlation between tumor cell genotype and disease progression and outcome.

Detection of specific abnormalities and DNA probes preparation in cancer cell lines is described in Example 1 and FIG. 1. Clinical application of the assay is expected. In collaboration with scientists at the Hormone Receptor Laboratory, University of Louisville (U Louisville), KY, (Dr. James Wittliff, P.I.), we will select tissue specimens obtained from breast cancer patients for which extensive follow-up data is available, and investigate whether ErbB gene alterations besides estrogen and progesterone receptor status ('ER and PR status') are important prognostic parameters.

EXAMPLE 3

Using Genetic Barcodes to Detect Gene Status in Cell Lines

We also began investigating chromosomal rearrangements in breast cancer cell lines. We now have FISH probe sets (2-3 colour) for several additional cancer/disease associated genetic loci (in addition to the previous ones for the ErbB 1, ErbB2, AURKA and RET loci).

Figure 9A:
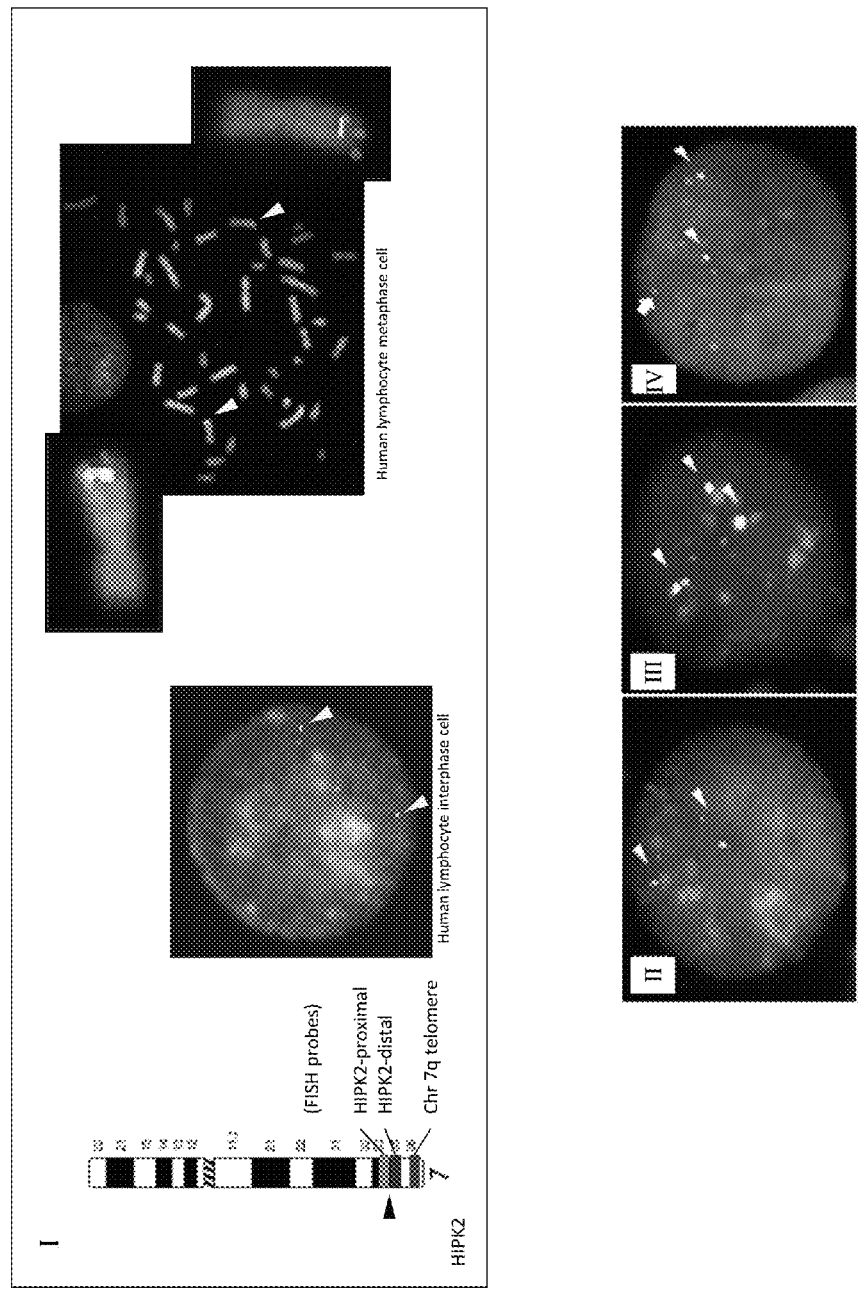
FIGS. 9A, 9B, and 9C—Shown are FISH probe sets (2-3 colour) for several additional cancer/disease associated genetic loci A) HIPK2, B) PTEN, C) XPG/ERCC5 (in addition to the previous ones for the ErbB1, ErbB2, AURKA and RET loci).
Figure 9B:
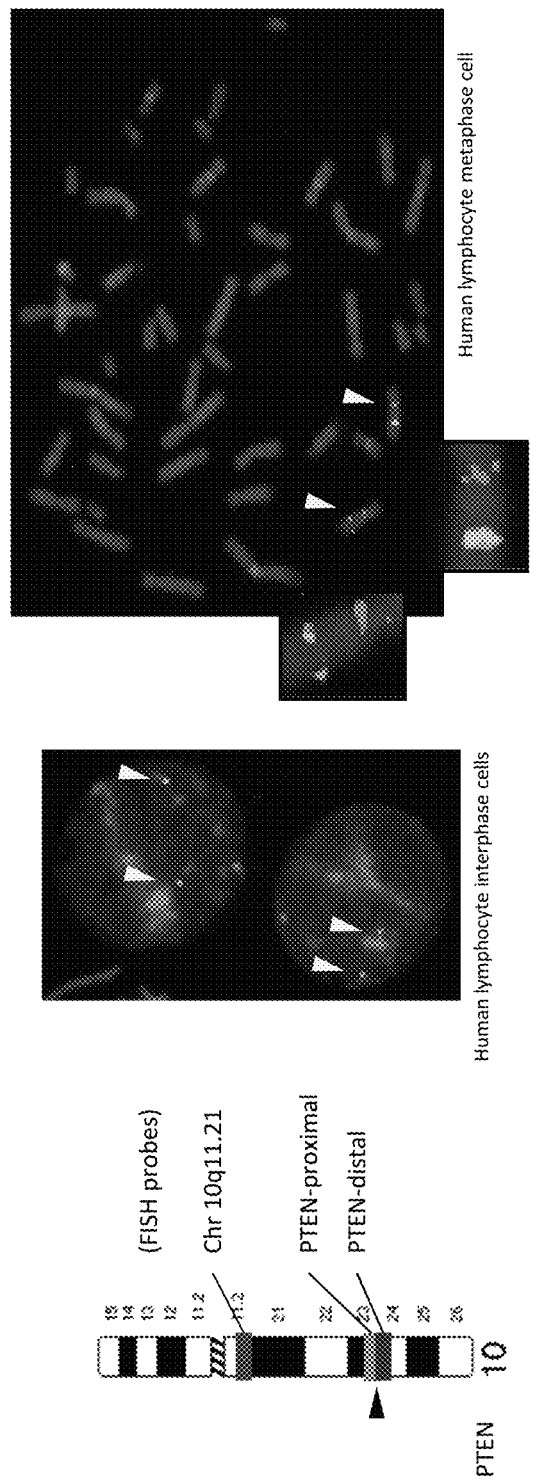
Figure 9C:
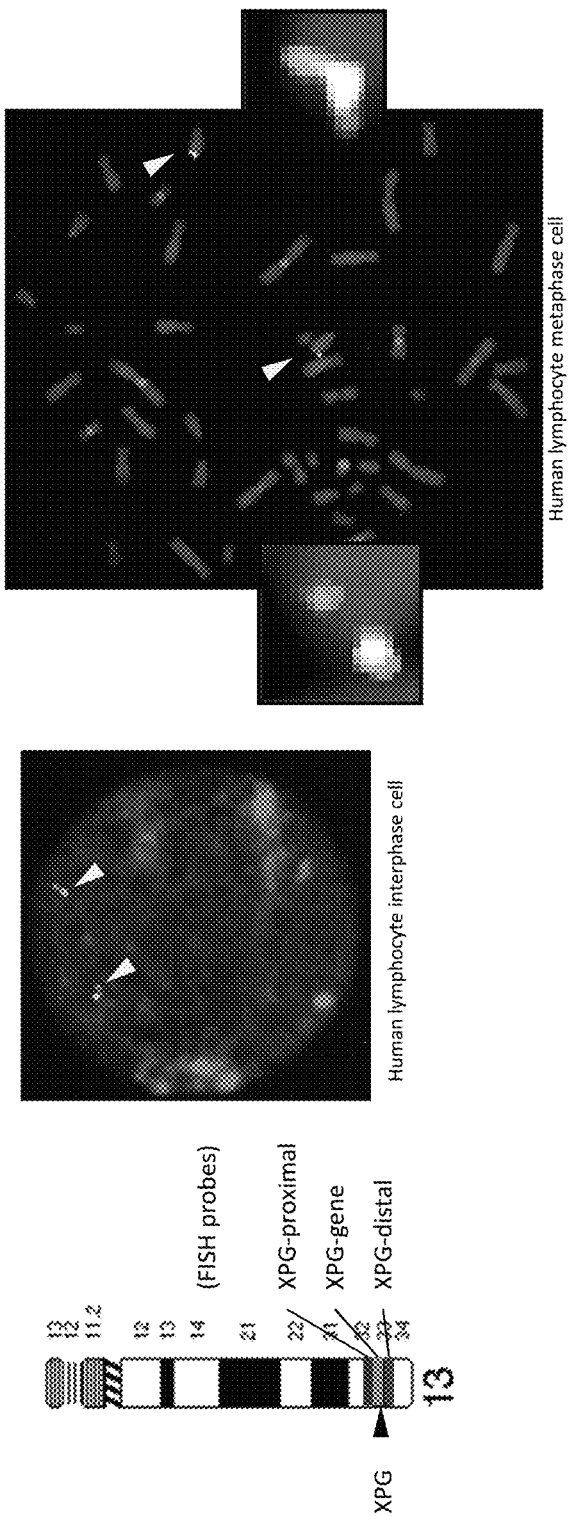

FIGS. 9A, 9B and 9C show examples of analyzing the A) HIPK2, B) PTEN, and C) XPG/ERCC5 gene loci. FIGS. 9A and 9B show the Homo Sapiens homeodomain interacting protein kinase 2 (HIPK2) gene locus in interphase cell nuclei, a protein kinase implicated in cancer chemoresistance, through either regulation of p53 mediated apoptosis or HIF1A mediated angiogenesis and cellular proliferation. This serine/threonine kinase involved in a preapoptotic pathway is a possible cancer therapy target, since it was found rearranged in 40-60% of various human cancers (Yu, J.; Deshmukh, H.; Gutmann, R. J.; Emnett, R. J.; Rodriguez, F. J.; Watson, M. A.; Nagarajan, R.; Gutmann, D. H. Alterations of BRAF and HIPK2 loci predominate in sporadic pilocytic astrocytoma. *Neurology* 2009, 73 (19), 1526-31).

FIG. 9A panels I, II, III and IV show BAC contig analysis of the HIPK2 locus. I) Three BAC contig probes were designed to overlap the HIPK2 locus and provide a tag for the telomeric end of chromosome 7q. II) Analysis of human lymphocytes from a normal individual shows 98% of them having the normal expected 2-2-2 pattern of the 3 contigs (arrowheads). III) Breast cancer cell line MDA-MB-468 is a heterogeneous population in which 33% of cells have a complete amplification/duplication of all three regions whereas IV) another breast cancer cell line (MDA-MB-231) is composed of 18% of cells with an extra copy of just one part (HIPK dist: exon 1) of the HIPK2 gene (arrow).

BAC-derived DNA probes are preferred due to low frequency of chimerism and ease of handling. We routinely prepare BAC DNA probes for chromosome enumeration, detection of deletions or gene amplifications in tumor specimens or delineation of chromosome breakpoints [57,58]. Based on publicly accessible high resolution physical maps at the Natl. Cancer Institute (NCI), the Natl. Center for Bioinformatics (NCBI) or UC Santa Cruz, most of the BAC probes are selected from either the RP-11 library prepared in the lab. of Dr. Pieter deJong at Roswell Park Cancer Institute, Rochester, N.Y. (now at the Children's Hospital Oakland Research Institute (CHORI), Oakland, Calif.), or the CTB and CTD BAC libraries prepared at the California Institute of Technology, Pasadena, Calif. (Caltech). The Weier lab at LBNL has copies of RP-11, plates 1-576 (384-well plates representing a 12.5-fold coverage of the human genome) and 423 384-well plates with BAC clones from CTD. In addition, the Weier lab acquired a copy of the 1 Mbp-spaced human BAC library from the Sanger Center, UK [66,67]. These libraries should provide more than enough BAC clones to cover multiple chromosomal regions. If additional clones are needed, they can be purchased from Invitrogen, Carlsbad, Calif. and used as described herein.

References

Grifo J A, Boyle A, Fischer E, Lavy G, DeCherney A H, Ward D C, Sanyal M K. Abstract Preembryo biopsy and analysis of blastomeres by in situ hybridization. Am J Obstet Gynecol. 1990 December; 163(6 Pt 1):2013-9.

Grifo J A, Boyle A, Tang Y X, Ward D C. Preimplantation genetic diagnosis. In situ hybridization as a tool for analysis. Arch Pathol Lab Med. 1992 April; 116(4):393-7.

Speicher M R, Gwyn Ballard S, Ward D C. Karyotyping human chromosomes by combinatorial multi-fluor FISH. Nat Genet. 1996 April; 12(4):368-75.

Cassel, M. J., Munné, S., Fung, J., Weier, H.-U. G. (1997) Carrier-specific breakpoint-spanning DNA probes for pre-implantation genetic diagnosis [PGD] in interphase cells. Hum Reprod 12:101-109

Fung, J., Munné, S., Duell, T., Weier, H.-U. G. (1998) Rapid Cloning of Translocation Breakpoints: from Blood to YAC in 50 Days. J Biochem Mol Biol Biophys 1:181-192

Fung, J., Hyun, W., Dandekar, P., Pedersen, R. A., Weier, H.-U. G. (1998) Spectral Imaging in Preconception/Preimplantation Genetic Diagnosis (PGD) of Aneuploidy: Multi-Colour, Multi-Chromosome Screening of Single Cells. J Ass Reprod Genet 15:322-329

Munné, S., Fung, J., Cassel, M. J., Márquez, C., Weier, H.-U. G. (1998) Preimplantation Genetic Analysis of Translocations: Case-Specific Probes for Interphase Cell Analysis. Human Genetics 102:663-674.

Weier, H.-U. G., Munné S., Fung J. (1999) Patient-specific Probes for Preimplantation Genetic Diagnosis (PGD) of Structural and Numerical Aberrations in Interphase Cells. Journal of Assisted Reproduction and Genetics 16:182-189

Weier, H. U. G., S. Munné, R. A. Lersch, C. Marquez, J. Wu, R. A. Pedersen, J. Fung. (1999) High performance analysis of single interphase cells with custom DNA probes spanning translocation breakpoints. Proc. of SPIE 3604: 227-236

Fung, J., H. U. G. Weier, J. D. Goldberg, R. A. Pedersen (1999) Simultaneous scoring of 10 chromosomes (9, 13, 14, 15, 16, 18, 21, 22, X, Y) in interphase nuclei by using Spectral Imaging. Proc. of SPIE 3604:218-226

Fung J., Munné S., Garcia J., Kim U.-J., Weier H.-U. G. (1999) Reciprocal translocations and infertility: molecular cloning of breakpoints in a case of constitutional transcolation t(11;22)(q23;q11) and preparation of probes for pre-implantation genetic diagnosis (PGD). Reproduction, Fertility and Development 11, 17-23.

Weier H.-U. G., Smida J., Zitzelsberger H., Lersch R. A., Hung J., Hsieh H. P., Salassidis K., McNamara G., Pedersen R. A., Fung J. (2000) Cytogenetic Analysis of Interphase Cells using Spectral Imaging Technology. Proc. of SPIE 3920:76-85

Lin, S. D., Cooper P., Fung J., Weier, H. U., Rubin E. M. (2000) Genome scan identifies a locus affecting gamma-globulin levels in human beta-cluster YAC transgenic mice. Mamm Genome 11:1024-1029

Lersch R. A., J. Fung, S. Munné, R. A. Pedersen, H.-U. G. Weier (2000) Case-specific, breakpoint-spanning DNA probes for analysis of single interphase cells. Genetic Testing 4:273-278

Fung J, Weier H-U G, Goldberg J D, Pedersen R A (2000) Multilocus genetic analysis of single interphase cells by Spectral Imaging. Hum Genetics 107:615-622

Fung, J., S. Munné, H. U. G. Weier (2001) Detection of Chromosome Translocation Products in Single Interphase Cell Nuclei. Methods in Cell Biology, Vol. 64, Part B, Cytometry, Third Edition (Z. Darzynkiewicz, H. A. Chrissman and J. P. Robinson, Eds.) Academic Press, San Diego, pp. 98-117

Fung J, Weier H-U G, Pedersen R A (2001) Detection of Structural and Numerical Chromosome Abnormalities in Interphase Cells Using Spectral Imaging. J Histochem Cytochem 49:797-798

Weier, H.-U.G., Munné, S., Lersch, R. A., Hsieh, H. B., Smida, J., Chen, X.-N., Korenberg, J. R., Pedersen, R. A., Fung J. (2001) Towards a Full Karyotype Screening of Interphase Cells: FISH and ChipTechnology. Molecular and Cellular Endocrinology 183, Suppl 1:S41-45

Fung J, Weier H-U G, Pedersen R A, Zitzelsberger H F (2002) Spectral Imaging Analysis of Metaphase and Interphase Cells. In: FISH Technology. B. Rautenstrauss and T. Liehr (Eds.), Springer Verlag, Heidelberg, pp. 363-387

Zitzelsberger H F, O'Brien B, Weier HUG (2002) Multicolor FISH techniques for the detection of inter- and intrachromosomal rearrangements. In: FISH Technology. B. Rautenstrauss and T. Liehr (Eds.), Springer Verlag, Heidelberg, pp. 408-424

Weier H-U G, Greulich-Bode K M, Ito Y, Lersch R A, Fung J (2002) Fluorescence in situ hybridization (FISH) in cancer diagnosis and prognostication: from the cause to course of the disease. Expert Review in Molecular Diagnostics 2(2): 109-119.

Liehr, T.; Weise, A.; Heller, A.; Starke, H.; Mrasek, K.; Kuechler, A.; Weier, H.-U. G.; Claussen, U. (2002) Multicolor chromosome banding (MCB) with YAC/BAC-based probes and region-specific microdissection DNA libraries. Cytogenet Genome Res 97:43-50

Weier H-U G, Weier J F, Oter Renom M, Zheng X, Colls P, Nureddin A, Pham C D, Chu L W, Racowsky C, Munné S (2005) Fluorescence in situ Hybridization (FISH) and Spectral Imaging (SIm) Analysis of Human Oocytes and First Polar Bodies. J Histochem Cytochem 53: 269-272

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

What is claimed is:

1. A method for uniquely labeling a cancer gene of interest in an individual cell nucleus, comprising the steps of:
    (a) obtaining and providing a single cell from a patient;
    (b) treating the single cell and fixing it to a substrate for analysis to increase accessibility of a target chromosome and to reduce nonspecific binding;
    (c) hybridizing a set of three probes to uniquely label the cancer gene of interest in a target chromosome, wherein a first probe is selected to hybridize to the region proximal to the cancer gene on the target chromosome, the second probe is selected to hybridize to the cancer gene of interest, and the third probe is selected to hybridize to the region distal to the cancer gene of interest on the target chromosome,
    wherein the set of the three probes provides a unique label for the cancer gene of interest in the individual cell nucleus, and wherein the cancer gene of interest is at least one of Erbb1, Erbb2, HIPK2, PTEN and XPG genes in tumor cells.

2. The method of claim 1, wherein the three probes are different in size.

3. The method of claim 1, wherein the three probes are labeled differently from each other.

4. The method of claim 1 wherein the parameters of pattern, size, arrangement and color of the labels provide the unique label of the gene of interest and any detected change in the unique label is an indicator of chromosomal changes such as addition, deletion, amplification, rearrangement and/or translocation.

5. The method of claim 1, further comprising the step of providing more than one set of chromosome-specific probes to analyze chromosomal changes in genes in tumor cells in human chromosome 4, 7, 10 and 13.

6. The method of claim 5, wherein the set of chromosome-specific probes comprising a set of three probes each to detect Erbb1, Erbb2, HIPK2, PTEN and XPG genes in tumor cells.

7. A method to detect amplification of a cancer gene, comprising the steps of:
    (a) obtaining and providing a single cell from a patient;
    (b) treating the single cell and fixing it to a substrate for analysis to increase accessibility of a target chromosome and to reduce nonspecific binding;
    (c) providing a set of three probes to detect the amplification of a cancer gene in a target chromosome, wherein a first probe is selected to hybridize to the proximal region of the cancer gene on the target chromosome, the second probe is selected to hybridize to the cancer gene, and the third probe is selected to hybridize to the distal region of the cancer gene on the target chromosome;
    (d) hybridizing the probes to the target chromosomes in the single cell;
    (e) removing unbound probes; and
    (f) detecting the hybridized probes to the target chromosomes, wherein the detection is carried out such that amplification of the cancer gene is detected if hybridization of at least one of probes is detected two or more times.

8. The method of claim 7, further comprising providing two sets of three probes to detect amplification of two cancer genes.

TABLE 1

| Human Mammary Epithelial Cell lines (HMECs) molecular subtype | ErbB1 | | | | | ErbB2 | | | | |
|---|---|---|---|---|---|---|---|---|---|---|
| | Gene Copy Number | Gene Expression | | | | Gene Copy Number | Gene Expression | | | |
| | FISH # foci[1] | SNP6 arrays[2,3] | RNAseq[2,3] | Exon arrays[2,3] | U133 arrays[2,3] | FISH # foci[1] | SNP6 arrays[2,3] | RNAseq[2,3] | Exon arrays[2,3] | U133 arrays[2,3] |
| MCAF10A (non-malignant) ER-/PR-/HER2(ErbB2)- | x2 | 0.244 | 785 | 9 | 5.17 | x2 | −0.071 | 163 | 8.66 | 3.46 |
| MDA-MB-231 (invasive ductal carcinoma) ER-/PR-/HER2(ErbB2)- | x5 | 0.306 | 433 | 9.16 | 4.18 | x3:x4 (1:1) | 0.11 | 135 | 7.38 | 3.61 |
| MDA-MB-468 (invasive ductal carcinoma) ER-/PR-/HER2(ErbB2)- | Large signal, single foci are not discernible | 1.978 | N/A | 10.31 | 8.8 | x2 | −0.207 | N/A | 8.14 | 4.08 |

[1] indicates the predominant foci signal pattern in the cell population
[2] RNAseq, SNP6, Affymetrix Exon array and U133 oligonucleotide gene array data kindly provided by Dr. J. Gray (Oregon Health and Science Univ)
[3] data are normalized copy number or gene expression levels 9. The method of claim 7, further comprising the steps of:
(g) removing the hybridized probes from the target chromosomes;
(h) repeating steps (a) through (g) for a second and third subset of probes,.

10. The method of claim 7 in which the detecting step is performed using a filter-based fluorescent microscope, optionally equipped with a spectral imaging system.

11. The method of claim 7 in which the detecting step is performed on interphase, non-proliferating or resting cells or organelles.

12. The method of claim 7 in which the detecting step is performed on metaphase cells.

* * * * *